US012705390B2

(12) United States Patent
Peake et al.

(10) Patent No.: US 12,705,390 B2
(45) Date of Patent: Aug. 11, 2026

(54) PRIVACY-AWARE DATA TRANSFORMATIONS

(71) Applicant: ResMed Pty Ltd, Bella Vista (AU)

(72) Inventors: Gregory Robert Peake, Sydney (AU); Michael C. Hogg, Sydney (AU); Hongjiang Yu, Sydney (AU)

(73) Assignee: ResMed Pty Ltd, Sydney (AU)

( * ) Notice: Subject to any disclaimer, the term of this patent is extended or adjusted under 35 U.S.C. 154(b) by 216 days.

(21) Appl. No.: 18/062,230

(22) Filed: Dec. 6, 2022

(65) Prior Publication Data

US 2023/0195936 A1 Jun. 22, 2023

Related U.S. Application Data

(60) Provisional application No. 63/265,677, filed on Dec. 17, 2021.

(51) Int. Cl.
*G06F 21/62* (2013.01)
*G16H 10/60* (2018.01)

(52) U.S. Cl.
CPC ......... *G06F 21/6254* (2013.01); *G16H 10/60* (2018.01)

(58) Field of Classification Search
CPC .. G06F 21/6254; G06F 21/6245; G06F 21/32; G16H 10/60; G16H 30/40; G16H 20/40; G16H 40/40; G06N 5/047; G06N 20/00; G06V 40/171
See application file for complete search history.

(56) References Cited

U.S. PATENT DOCUMENTS

| | | | | |
|---|---|---|---|---|
| 11,935,252 | B2 * | 3/2024 | Peake | G16H 10/20 |
| 2012/0245962 | A1 * | 9/2012 | Smith | G07F 17/0092 705/2 |
| 2014/0064588 | A1 * | 3/2014 | Su | G06T 7/0012 382/131 |
| 2017/0173289 | A1 * | 6/2017 | Lucey | A61B 5/1079 |
| 2019/0103190 | A1 * | 4/2019 | Schmidt | G16H 50/50 |
| 2020/0105400 | A1 * | 4/2020 | Alvelda, VII | G06V 10/26 |
| 2022/0092798 | A1 * | 3/2022 | Peake | G16H 40/60 |
| 2022/0253592 | A1 * | 8/2022 | Rao | G16H 30/20 |
| 2023/0178218 | A1 * | 6/2023 | Papaioannou | G16H 30/40 382/128 |

FOREIGN PATENT DOCUMENTS

| | | | | |
|---|---|---|---|---|
| CN | 213819960 U * | 7/2021 | | |
| WO | WO-2021097331 A1 * | 5/2021 | | A61M 16/0605 |

OTHER PUBLICATIONS

European Patent Office, Extended European Search Report for Application 22214013.9-1126 dated Aug. 5, 2023.

* cited by examiner

*Primary Examiner* — Mohammed Waliullah
(74) *Attorney, Agent, or Firm* — Patterson + Sheridan, LLP

(57) ABSTRACT

Techniques for data security are provided. Face data for a patient is received, where the face data is linked to an identifier of the patient. A suggested medical device is determined by processing the face data using a recommendation model. Therapy data stored in a first data store and equipment data stored in a second data store are identified based on the identifier, where the equipment data indicates an actual medical device that was provided to the patient. The suggested medical device, the therapy data, and the equipment data are associated.

22 Claims, 15 Drawing Sheets

PRIVACY-AWARE DATA TRANSFORMATIONS

CROSS-REFERENCE TO RELATED APPLICATIONS

This application claims benefit of U.S. provisional patent application Ser. No. 63/265,677 filed Dec. 17, 2021. The aforementioned related patent application is herein incorporated by reference in its entirety.

INTRODUCTION

Aspects of the present disclosure relate to privacy-aware computing. More specifically, aspects of the present disclosure relate to de-identifying, linking, and evaluating user data in a privacy preserving fashion.

In a wide variety of medical (and non-medical) settings, accurate facial measurements are needed to drive decisions and selections for the user. For example, in many cases, the particular dimensions of the face of the individual user are needed to help design, construct, and/or select an appropriate mask that will fit the user's face comfortably and completely. As one example, continuous positive airway pressure (CPAP) machines generally use a mask or nosepiece to deliver constant and steady air pressure to users during sleep. For the system to operate properly (as well as to improve the user experience and health), it is important that the mask fit properly (e.g., comfortably, and without leaks around the face). Often, the face dimensions (and other user data) are collected and stored in one more repositories.

In many environments, a wide variety of other user data is similarly stored for analysis, future reference, recordkeeping, and the like. Maintaining such user data has a number of privacy implications, as well as diverse regulatory and legal frameworks intended to safeguard the user's data. For example, in many cases, identifiable user data (e.g., data that personally or uniquely identifies the user) must be kept secure, and the analysis and evaluation that can be performed using the data (e.g., to train a machine learning model) can be severely limited by such regulations.

Additionally, though various user data may be stored across multiple repositories or systems, there are often safeguards in place to prevent the data from being correlated or linked for collective analysis, such as due to the above-discussed regulatory landscape.

Improved systems and techniques to maintain user privacy and data security are needed.

SUMMARY

According to one embodiment presented in this disclosure, a method is provided. The method includes: receiving face data for a first patient, wherein the face data is linked to a first identifier of the first patient; determining a suggested medical device by processing the face data using a recommendation model; identifying, based on the first identifier, therapy data stored in a first data store; identifying, based on the first identifier, equipment data stored in a second data store, wherein the equipment data indicates an actual medical device that was provided to the first patient; and associating the suggested medical device, the therapy data, and the equipment data.

According to a second embodiment of the present disclosure, a method is provided. The method includes: accessing, by a user device, a patient survey via a provided link for a first patient; providing a set of responses for the patient survey, wherein the set of responses facilitate selection of a mask for the first patient; generating face data by performing a facial scan of the first patient using one or more cameras of the user device; transmitting the face data, along with the set of responses, to a mask selection component, wherein: the mask selection component uses the face data and set of responses to select the mask for the first patient; and one or more non-identifying aspects of the face data are linked with therapy data for the first patient and equipment data for the first patient.

According to a third embodiment of the present disclosure, a system is provided. The system includes: a user device configured to perform an operation comprising: collecting, from a first patient, survey data; and determining, using on one or more imaging devices, face data for the first patient. The system further includes a mask selector component configured to perform an operation comprising: receiving the face data for the first patient; and selecting a suggested facial mask based on the face data. The system also includes a first data store configured to store the survey data and the face data for the first patient; a second data store configured to store therapy data for the first patient, wherein the therapy data indicates patient compliance with one or more prescribed therapies; a third data store configured to store equipment data for the first patient, wherein the equipment data indicates an actual facial mask provided to the first patient; and a linking component configured to perform an operation comprising: de-identifying the face data, such that the face data does not uniquely identify the first patient; and linking the de-identified face data, the therapy data, and the equipment data.

According to a fourth embodiment presented in this disclosure, a method is provided. The method includes: receiving de-identified face data associated with a first patient, wherein the de-identified face data does not uniquely identify the first patient; and determining a suggested medical device by processing the de-identified face data using a recommendation model.

According to a fifth embodiment presented in this disclosure, a method is provided. The method includes: receiving de-identified face data associated with a first patient, wherein the de-identified face data does not uniquely identify the first patient; identifying, based on a first identifier associated with the de-identified face data, patient data stored in a first data store; and associating the de-identified face data and the patient data.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
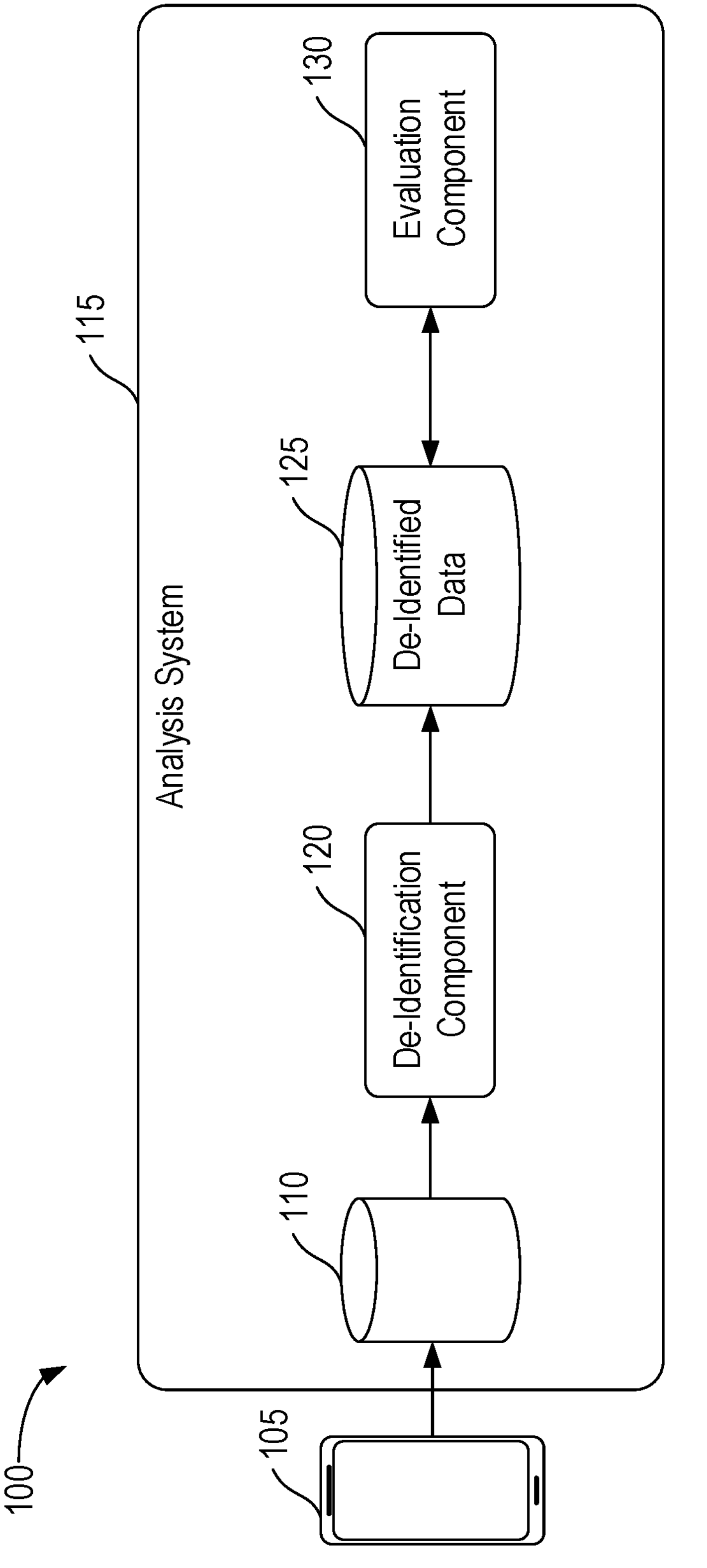
FIG. 1 depicts an example environment to de-identify user data and to analyze the de-identified data for a variety of tasks.

Aspects of the present disclosure provide apparatuses, methods, processing systems, and computer-readable mediums for improved user privacy and data security.

User data can be stored in a variety of systems or repositories for a variety of purposes. Often, at least some of this data can be used to identify the user. As used herein, data is considered "identifying" if it uniquely identifies the user, or identifies a small set of users (e.g., less than five). For example, a user's birthdate, name, and location are collectively identifying. Similarly, an image of the user's face, a three-dimensional mesh of the face, and the like are identifying. As used herein, data is considered "non-identifying" if it does not personally identify the user (or corresponds to a sufficiently large set of users). For example, a relatively limited set of measurements for the user's face (e.g., nose depth, face height, and the like) generally do not identify the user, as a significant number of users will share the same (or similar) measurements for these values.

In some embodiments, data can be "de-identified" using various processes described in more detail below. As used herein, a "de-identifying" operation generally involves receiving some identifying user data, and performing one or more operations (such as transformations, measurement extractions, and the like) to yield de-identified data (e.g., non-identifying data). These de-identification steps may be applied in a variety of points in the pipeline, enabling data to be collected, correlated, linked, aggregated, and evaluated for a variety of purposes (such as training machine learning models) while maintaining user privacy and data security.

In some embodiments, different user data is maintained in multiple different repositories. For example, a tool may be used to collect face data (e.g., facial measurements) of a user, a device or object can be selected based on these measurements, and data relating to the measurements and/or suggested device can be stored in a first repository. As one example, the face data can be used to select, design, modify, or otherwise facilitate provisioning of a medical device, such as a CPAP mask. Although masks or medical devices are discussed in some examples, embodiments of the present disclosure are readily applicable to a variety of objects or devices, such as headsets, virtual reality (VR) or augmented reality (AR) goggles, headphones, eyewear, and the like.

In one embodiment, another repository can include patient data relating to the medical equipment. For example, this second repository may store data indicating which device(s) were provided to each user, resupply information, and the like. That is, while the first repository can store data relating to face shape and suggested devices, the second repository may store supply data indicating what device(s) were actually given to the patient. Further, a third repository may include therapy or compliance data for one or more users. For example, the therapy data may indicate whether the user has any reported problems or issues with their provided device(s), how often the user uses the device (e.g., what percentage of evenings the user uses a CPAP mask), and the like.

In some embodiments, managing users (e.g., healthcare providers) can use these systems and repositories to evaluate user compliance or adherence to a treatment plan. However, as discussed above, these separate systems are often maintained independently, and there may be a variety of regulatory or legal frameworks that prevent the data from being aggregated for analysis, evaluation, or other processes. For example, one tool may recommend a specific face mask based on user measurements, while a second tool monitors compliance and performance of assigned devices (e.g., the amount of air leak for a CPAP mask). However, as these systems are kept separate, the healthcare provider cannot readily determine whether the mask selection tool is operating effectively (e.g., whether the suggested mask fits well, as indicated by the therapy or compliance data). Similarly, the provider is unable to determine whether the provided device (which may be indicated in an equipment data store) matches the suggested device. That is, the healthcare professional cannot readily determine whether the equipment provider followed the recommendation.

Embodiments of the present disclosure provide techniques to merge a variety of disparate data in a way that preserves user privacy and data security, enabling additional analyses and evaluations to be performed on the aggregated set. Further, the merged data can be safely used for other purposes, such as training a machine learning model, enabling significantly improved inferences (e.g., due to a wider set of input training data) while maintaining user privacy. This can drastically improve the operations of these models and other systems, as they learn to perform more accurately using more robust and complete data sets.

Example Environment for De-Identifying and Analyzing User Data

FIG. 1 depicts an example environment 100 to de-identify user data and analyze the de-identified data for a variety of tasks.

In the depicted environment 100, a user device 105 provides data to an analysis system 115. In the illustrated example, the user device 105 is a smartphone. In embodiments, however, the user device 105 can include any suitable computation device, including a laptop, desktop computer, tablet, and the like. Generally, a user of the user device 105 (e.g., a patient) may use the user device 105 to transmit any user data to the analysis system 115, such as survey data (e.g., answering questions to secure care or medical devices, such as a sleep schedule, concerns or issues with medical devices, and the like), face data (e.g., face images or measurements), and the like.

In some embodiments, the user device 105 transmits this data in response to a request from the analysis system 115 or other entity. For example, a healthcare provider may transmit a link to the user (via the user device 105), enabling the user to open the link and provide the requested data, which is securely uploaded to the analysis system 115. Although the illustrated environment 100 includes a user device 105 providing this data, the data provided to the analysis system 115 can be received from a wide variety of sources, such as a device used by a healthcare professional, other storage repositories, and the like.

In at least one embodiment, the received data includes face data of the user. As used herein, "face data" generally includes data indicative of facial measurements or characteristics, and can include the measurements themselves (e.g., nose depth, eye width, etc.), coordinates of landmarks or points on the user's head and/or face, one or more images of the user's face, one or more three-dimensional meshes generated by scanning the user's face, and the like. In some embodiments, the received data also indicates a suggested device (e.g., a specific CPAP mask) for the user. This suggested device may be determined, for example, by one or more components configured or trained to design, modify, or otherwise select a device based on the face data of the user. In some embodiments, the analysis system 115 itself performs this device selection using the face data.

As illustrated, the data received from the user device 105 is initially stored in a repository 110. For example, the repository 110 may include, for each user, a respective record indicating user data such as biographical information (e.g., the user's name, birthdate, location, and the like), a unique identifier or code (e.g., a user ID), face data (e.g., one or more images or meshes), and a device that was suggested for the user (e.g., using one or more trained machine learning models).

As discussed above, some or all of this data may be identifying of the user. For example, an image of the user's face will generally be considered identifiable. In the illustrated example, therefore, the analysis system 115 includes a de-identification component 120. Generally, the de-identification component 120 is configured to receive identifying user data (e.g., images of the user) and generate de-identified data 125 that does not uniquely identify the user. In embodiments, the particular techniques or operations used to de-identify the data may differ depending on the particular implementation, the characteristics of the identifying data, and the like.

In one embodiment, if the face data includes images of the user, the de-identification component 120 may de-identify these images to extract one or more facial measurements and/or landmarks for the user. As discussed above, these facial measurements and/or landmarks can generally be shared by a large number of people, allowing the de-identified face data to be used for further processing without impinging on the privacy of the user or the security of the data in the repository 110.

In some embodiments, the face data includes one or more three-dimensional meshes for the user's head or face. In at least one embodiment, the de-identification component 120 can de-identify this mesh by similarly extracting one or more facial measurements (such as face height, nose depth, and the like) and/or landmark coordinates (such as the coordinates of one or more points on the face) from the mesh. These simple measurements and/or landmarks can be provided or stored as the de-identified data 125, while the identifying three-dimensional mesh remains in the repository 110.

In some embodiments, the face data includes a three-dimensional mesh, and the de-identification operation involves modifying the mesh such that principal characteristics are retained (e.g., such that the nose depth and width, eye width, face height, and the like are the same or within a defined threshold of the original mesh), while identifying features are removed. For example, in one such embodiment, the de-identification component 120 can use principal component analysis (PCA) and one or more statistical shape models for the human face (e.g., indicating statistically average faces or heads) to morph the user's three-dimensional mesh into a non-identifying or generic mesh (that still includes the primary characteristics needed for subsequent analysis) for the user's face. In at least one embodiment, this morphing process is used to generate a set of values (e.g., a number or contribution for each principal component) that can be used, in conjunction with the statistical shape model, to reconstruct the user's face. Generally, the set of values may be meaningless without the shape model (e.g., they cannot be used to identify or reconstruct the user's face without also using the original statistical model). In one such embodiment, the resulting values may be maintained or stored separately from the statistical model (e.g., in separate repositories, on separate computing systems, and the like). In this way, having access to the statistical model alone (without access to the set(s) of values for each user) may not enable identification of the user. Similarly, accessing the sets of values themselves (without access to the original model) may not enable identification of the user.

Various aspects of this de-identification process are described in more detail below, such as with reference to FIGS. 3-7. Regardless of the particular operations used by the de-identification component 120, the de-identified data 125 can generally include non-identifying face data for one or more users. In some embodiments, the de-identified data 125 is still be linked or associated to the user in some way. For example, the de-identified data 125 may include user IDs for each user, allowing the analysis system 115 (or users of the system) to identify and retrieve the non-identifying face data for a given user. The de-identified data 125 is referred to as de-identified or non-identifying to indicate that the included face data itself does not uniquely identify the user.

As illustrated, the analysis system 115 can provide the de-identified data 125 to an evaluation component 130, which may perform a wide variety of operations, evaluations, or analyses using the de-identified data 125. In at least one embodiment, the evaluation component 130 uses the de-identified data 125 to select or suggest a mask or other device for the user. That is, in some embodiments, the repository 110 includes the face data, and the evaluation component 130 itself performs mask selection (after the de-identifying).

In one embodiment, the evaluation component 130 uses the de-identified data 125 to train or refine one or more machine learning models. That is, the analysis system 115 may train and/or use a machine learning model to process de-identified face data for a user in order to generate a wide variety of output (e.g., classifications or other values). For example, the evaluation component 130 may train a model that can predict, based on de-identified face data, one or more other attributes of the user. As another example, the evaluation component 130 may train a model to generate, select, optimize, modify, or otherwise provide a device selection for the user based on the de-identified face data (e.g., to suggest a proper CPAP mask).

In embodiments, the output of the evaluation component 130 may be stored in the analysis system 115 (e.g., in the de-identified data 125 or in the repository 110) or in one or more external repositories. Although the illustrated example includes a discrete de-identification component 120 and evaluation component 130, in embodiments, the operations and functionality of the analysis system 115 may be combined or distributed across any number of components and devices.

Figure 2:
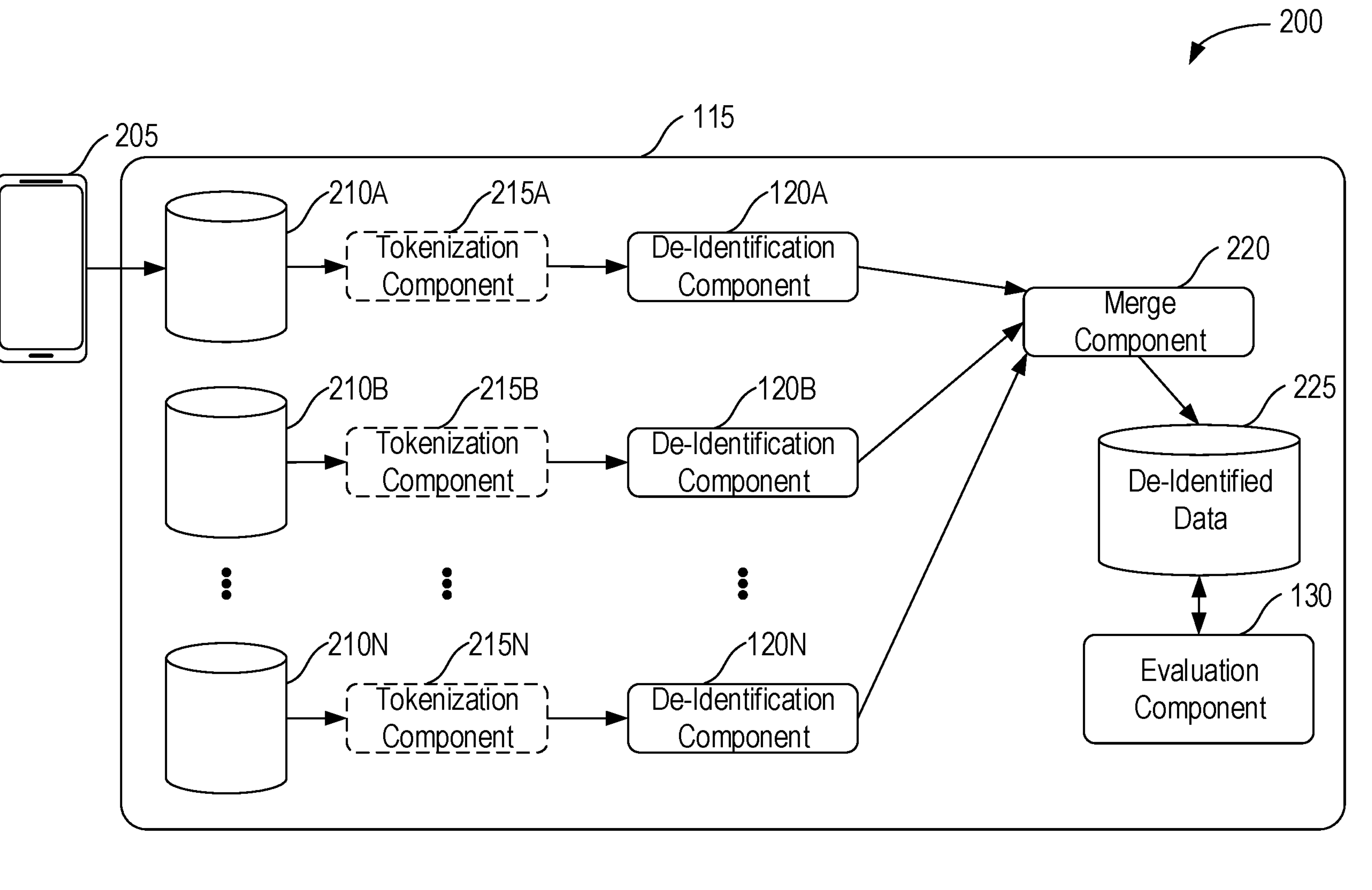
FIG. 2 depicts an example environment to de-identify user data, correlate various de-identified data, and to analyze the de-identified data for a variety of tasks.

Example Environment for De-Identifying, Correlating, and Analyzing User Data FIG. 2 depicts an example environment 200 to de-identify user data, correlate various de-identified data, and analyze the de-identified data for a variety of tasks.

In the depicted environment 200, a user device 205 provides data to the analysis system 115. In the illustrated example, the user device 205 is a smartphone. In embodiments, however, the user device 205 can include any suitable computation device, including a laptop, desktop computer, tablet, and the like. In a similar manner to the user device 105 of FIG. 1, the user of the user device 205 can generally use it to transmit any relevant user data to the analysis system 115, such as survey data (e.g., answering questions or providing data, such as a sleep schedule, concerns or issues with medical devices, and the like), face data (e.g., face images, measurements, or landmarks), and the like.

In some embodiments, as discussed above, the user device 205 transmits this data in response to a request from the analysis system 115 or other entity. For example, a healthcare provider may transmit a link to the user (via the user device 205), enabling the user to open the link and provide the requested data, which is securely uploaded to the analysis system 115. Although the illustrated environment 200 includes a user device 205 providing this data, the data provided to the analysis system 115 can be received from a wide variety of sources, such as a device used by a healthcare professional, other storage repositories, and the like.

In the illustrated environment 200, the received data includes face data of the user. As discussed above, the face data can generally include any data indicative of facial characteristics of the user, such as the measurements themselves (e.g., nose depth, eye width, etc.), coordinates of one or more facial landmarks (e.g., one or more points on the ear structures, one or more points no the nose structure, and the like) one or more images of the user's face, one or more three-dimensional meshes generated by scanning the user's face, and the like. As illustrated, the data received from the user device 205 is initially stored in a repository 210A.

In the illustrated example, the repository 210A can also indicate a suggested device (e.g., a specific CPAP mask) for each user. For example, the user's face data (or de-identified face data, as discussed above) may be processed by one or more components or systems (e.g., a mask selection component) to determine, design, modify, or otherwise select a device based on the face data of the user. In this way, the repository 210A can be used to store face data for each user, alongside an indication as to which device(s) and/or modification(s) were recommended based on the face data.

In the depicted embodiment, the repository 210B and repository 210N can similarly store some elements of user data for one or more users. For example, the repository 210B may store equipment data for the users. This equipment data may indicate, for example, which device(s) have been provided to each user, when each device was provided, what device(s) are currently in use by the user, resupply information (e.g., if use of the device or equipment requires periodic replenishment), and the like.

In some embodiments, the repository 210N includes therapy data for the users. The therapy data may generally indicate, for example, compliance data for each user (e.g., how often the user uses the prescribed device(s)), any potential issues, complaints, or problems with the device(s) (e.g., whether the user has indicated that their provided mask leaks air around their nose), and the like.

As discussed above, in some embodiments, there may be a variety of rules and frameworks (including regulatory rules, laws or statutes, company policies, and the like) that disallow directly combining the data from the repositories 210A-210N. For example, though the repository 210A may indicate what device was suggested or recommended for a user and the repository 210B may indicate what device was actually provided, there is no conventional component or system that correlates this data, which would allow for deeper and more insights and understanding.

For example, using conventional systems, a user (e.g., a healthcare provider) cannot determine whether the provided mask aligns with the recommended mask. Lacking this insight, the user cannot determine whether others are following the generated recommendations, and thus cannot determine whether the recommendation system (e.g., the underlying machine learning models) are generating accurate or optimized suggestions. Similarly, using conventional systems, a user may be able to see that a patient has complained about a poor fit of their provided mask (e.g., in repository 210N), but cannot determine what mask was provided (as this data is stored in repository 210B).

In an embodiment, therefore, the analysis system 115 enables the data to be de-identified and correlated to enable broader and more comprehensive analysis and evaluation of the disparate sets of data in each repository 210.

In the illustrated example, the data from each repository 210A-N is optionally tokenized by a respective tokenization component 215A-N. Generally, the process of tokenization involves obfuscating meaningful data (e.g., the user's name, birthdate, social security number, and the like) with a string of characters (referred to as a token) prior to further processing (e.g., matching or correlating data), enabling these processes to be performed without exposing potentially sensitive data while the original values are stored in a secure repository. After processing, the tokens can be replaced with the original data. For example, rather than matching data from different repositories based on the user's social security number (which may violate rules, laws, regulations, policies, and the like, and which may otherwise be relatively less secure), the tokenization components 215 may replace the social security with a token, and the system may correlate the data using these tokens. After correlation, the token can be replaced with the true value (e.g., the social security number).

In the illustrated example, the tokenization components 215A-N are depicted in dashed lines to indicate that they serve as an optional step in the process. In some embodiments, data may or may not be tokenized depending on the particular implementation and deployment. Additionally, some data may be tokenized (e.g., to obfuscate personal health information of the users) while other elements of data are not. Though a set of discrete tokenization components 215 (one for each repository 210) are depicted for conceptual clarity, the data from all repository 210 may be tokenized by a single tokenization component in some embodiments.

After undoing tokenization, in the illustrated example, the data from each repository 210A-N is processed by a respective de-identification component 120A-N. Though a set of multiple de-identification components 120 (one for each repository 210) are depicted for conceptual clarity, in some embodiments, a single de-identification component 120 may be used to process data from all of the repositories 210.

As discussed above, the de-identification component 120 generally de-identifies the data from repositories 210A-N. In some embodiments, as discussed above, only a subset of the data is de-identified. For example, the analysis system 115 may de-identify face data from repository 210A, but leave the remaining data unchanged.

Additionally, as discussed above, the particular operations or processes used to de-identify the data may vary depending on the nature of the original face data. For example, the de-identification component 120A may extract (non-identifying) facial measurements and/or landmarks from one or more images of the user, a three-dimensional mesh of the user, a video of the user, and the like. Similarly, the de-identification component 120A may morph or modify a three-dimensional mesh of the user's face into a non-identifying mesh having the same principal features (e.g., the same face height and nose depth). In some embodiments, as discussed above, the principal feature values (e.g., weights or contributions for each) for the specific user can be stored or maintained separately (e.g., in a different repository, or on an entirely different computing system) from the statistical model used to morph the face. This can further ensure privacy and security.

In the illustrated example, a merge component 220 can then identify and link (de-identified) records from each repository 210 to yield a set of linked de-identified data 225. Continuing the above example, the merge component 220 may link de-identified face data from the repository 210A with equipment data from repository 210B and/or therapy data from repository 210N to allow the relevant data from each user to be correlated. In embodiments, this linking or association may be performed using a variety of techniques. In at least one embodiment, the merge component 220 can use a unique identifier assigned to each user in order to match the relevant records from each repository. For example, the face data in repository 210A, equipment data in repository 210B, and therapy data in repository 210N may all be associated with the same patient ID, and the merge component 220 can link the de-identified data using this ID. In other embodiments, other entries (such as a combination of birthdate and name) can be used to correlate the data.

Notably, although some elements in the de-identified data 225 may identify the underlying user (e.g., using a name and date of birth), the face data itself is non-identifying. In at least one embodiment, the face data is de-identified due to various rules, regulations, or policies that apply to its use. For example, the user may grant permission to allow their face data to be stored and used within the repository 210A for some purposes (e.g., to provide a suggested device). However, such permission does not automatically extend use of the identifiable face data for other purposes (such as training a machine learning model). By de-identifying the face data into an anonymized or more generic form (e.g., a set of measurements, a set of landmarks, and/or a morphed mesh), the analysis system 115 is able to use the data for further processing and operations while remaining compliant with various laws and regulations, such as the Health Insurance Portability and Accountability Act (HIPAA), the General Data Protection Regulation (GDPR), and the like.

In embodiments, this merged set of de-identified data 225 can be used to drive a wide variety of analyses, processes, and operations. For example, as discussed above, the evaluation component 130 may use the merged de-identified data 225 to train one or more machine learning models, or to perform other aggregated analysis on the user data.

In one embodiment, the evaluation component 130 can determine whether the suggested device (indicated in the data stored in repository 210A) matches the device that was actually provided to the user (indicated in the data stored in repository 210B). If not, a variety of remedial actions may be appropriate, such as generating and/or transmitting an alert or request (e.g., to the equipment provider) inquiring as to why the recommendation was not followed. Depending on the response, the evaluation component 130 can continue to take a number of actions.

As one example, if the equipment provider indicates that the suggested device was inapt, the evaluation component 130 can refine or revise the recommendation model(s). If the provider indicates that they were not aware of the suggestion, the system (or user) may take steps to ensure that the recommendations are more apparent to the equipment providers.

As an additional example, the evaluation component 130 may transmit an alert to the user (e.g., the patient using the device) to inform them that they are using a different device than the one that was recommended, thereby allowing the user to potentially request an appropriate device and improve their experience.

Generally, the merged de-identified data 225 can be used for a wide variety of computational operations. As discussed above, the techniques described herein enable otherwise identifiable face data to be de-identified and used for additional purposes and goals, supporting additional functionality that was not previously-available. Further, by merging de-identified data from multiple sources, the insights and detail that can be gleaned (e.g., using machine learning) are significantly expanded, resulting in improved models that can generate more accurate output in more diverse problem spaces.

Example User Interface for Collecting De-Identified Face Data

Figure 3:
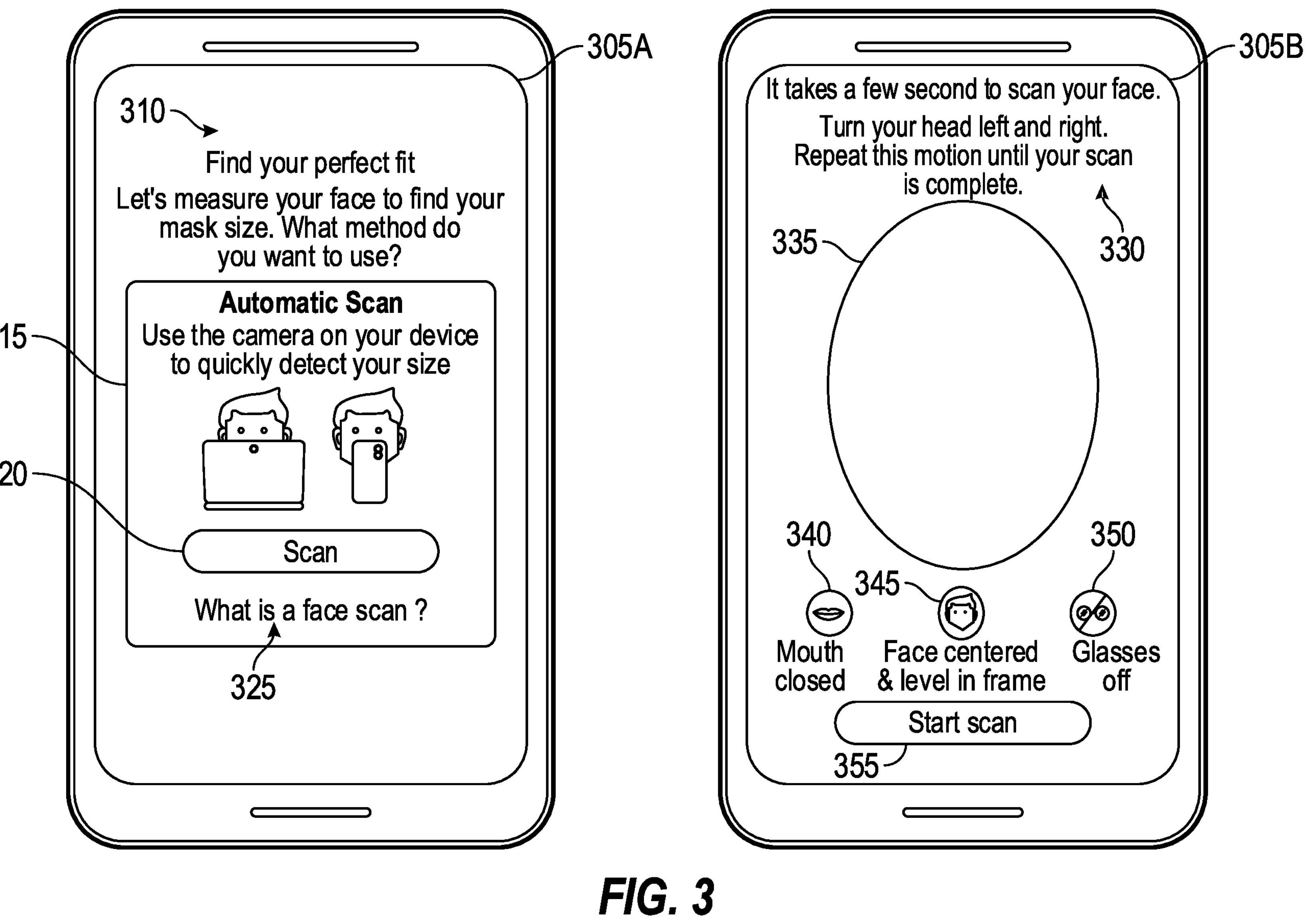
FIG. 3 depicts an example user interface for collecting de-identified face data.

FIG. 3 depicts an example user interface 305 for collecting de-identified face data. In one embodiment, the user interface 305 is output via a user device (e.g., user device 105 of FIG. 1 or user device 205 of FIG. 2) to facilitate collection of face data.

In at least one embodiment, the user interface 305 is displayed upon the user taking some action in response to a communication from a healthcare provider or administrator. For example, a doctor my cause a link to be sent to the user's device, asking the user to provide face data (and, in some aspects, other biographical data). Upon selecting the link, in one such embodiment, the interface 305A is displayed.

The interface 305A generally provides information relating to what data is needed, and how it can be collected. Specifically, in the portion 310, the interface 305A indicates that the goal of the process is to measure the user's face to enable the proper mask size to be selected (e.g., for a CPAP machine). Although the illustrated example relates to mask selection, in embodiments, the interface 305 can be used for a variety of device selection or design.

As illustrated in portion 315, the interface 305A provides an option to allow the user to automatically scan their face, using the camera of the device to detect the facial measurements and/or landmark coordinates. In an embodiment, the system can use a two-dimensional camera on the user device (e.g., a webcam), and need not rely on three-dimensional cameras or scanners. In this example, the user can initiate the scan by selecting button 320, or ask for more detail on the scan by using button 325.

In the illustrated example, upon selecting the button, the interface 305B is displayed. This interface 305B generally provides instructions for how the scan is to be performed. Specifically, as indicated in block 330, the system instructs the user to turn their head from left to right until the scan is complete. In an embodiment, this angular motion allows the system to capture images with the user's head at various angles to the camera, enabling nose depth to be measured more accurately.

In some embodiments, portion 335 can generally include various cues to aid the user in the scanning process, including one or more images or videos of the scan being performed, or a live-feed of the user (e.g., via the user device's camera) to enable the user to center their face in the frame. In an embodiment, the indicators 340, 345, and 350 can indicate instructions to insure a successful scan, including that the mouth should be closed, the face should be centered and level, and glasses should be removed. In at least one embodiment, these indicators 340, 345, and 350 can selectively indicate whether these impedances are detected (e.g., by lighting up when the system detects that the user is wearing glasses).

In some embodiments, the images are captured locally and transmitted, as identifying face data, to a remote device (e.g., to the analysis system 115 of FIG. 1). As discussed above, the system 115 can then de-identify this data. In at least one embodiment, the image(s) may be evaluated locally, on the user device, and the de-identified facial measurements and/or landmarks can be transmitted to the analysis system 115. In one such embodiment, even if the local device determines the measurements/landmarks, the images themselves can still be transmitted to the analysis system for storage and future use.

Example Method for De-Identifying and Evaluating User Data

Figure 4:
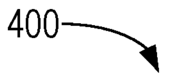
FIG. 4 is a flow diagram depicting an example method for de-identifying and evaluating user data.
Figure 4:
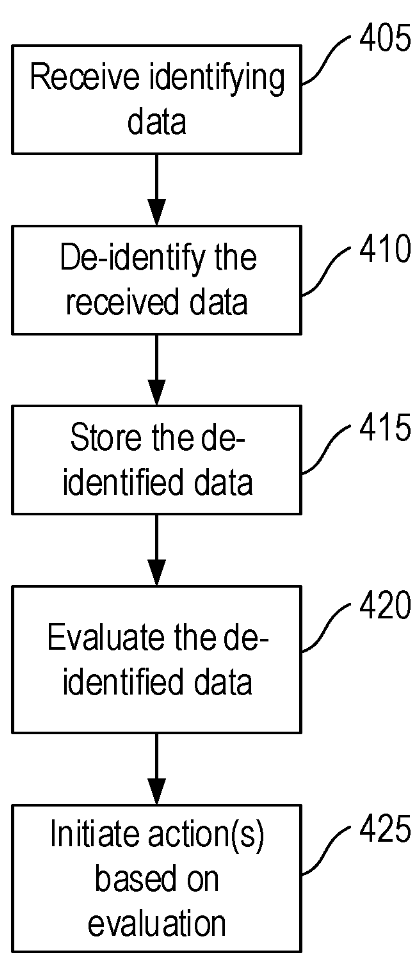

FIG. 4 is a flow diagram depicting an example method 400 for de-identifying an evaluating user data. In some embodiments, the method 400 is performed by an analysis system (e.g., analysis system 115 of FIGS. 1 and 2).

At block 405, the analysis system receives identifying data from one or more users (e.g., patients). In at least one embodiment, the identifying data includes face data of the user. As discussed above, this data is identifying in that it can uniquely identify the user (or identify a sufficiently small subset of users, such as when less than five or ten users "match" the face data). In some embodiments, the identifying data can include one or more images of the user's face, one or more three-dimensional meshes generated by scanning the user's face, and the like.

At block 410, the analysis system de-identifies the received data. As discussed above, there may be a variety of de-identifying techniques that can be used, depending at least in part on the characteristics of the identifying data. For example, if the face data includes images of the user, the analysis system may extract one or more facial measurements and/or landmark coordinates from these images (e.g., a nose depth, nose width, face height, and the like). As an additional example, if the identifying face data includes a three-dimensional mesh, the analysis system can similarly extract such facial measurements and/or landmark coordinates from the mesh. As discussed above, these facial measurements/landmarks are considered "non-identifying" because a large number of individuals generally share the same (or similar) values for these measurements/landmarks.

In some embodiments, if the identifying data includes a three-dimensional mesh, the analysis system can morph this mesh to a non-identifying form that preserves the principal measurements, shape, and/or structure of the user's face, while obscuring or removing identifying features. For example, as discussed above, the analysis system may use a set of statistical models of the human face, as well as PCA or other techniques, to morph the mesh into a non-identifiable form. In at least one embodiment, as discussed above, the original statistical model(s) may be maintained in a first repository, while the contributions or values determined or generated for the specific user may be stored or maintained in a second. This can ensure that an entity having access to the one repository (without access to the other) cannot reconstruct the user's face, thereby enhancing privacy and security.

At block 415, the analysis system stores the de-identified data in one or more repositories. For example, the analysis system may store the de-identified data in the de-identified data 125 repository (illustrated in FIG. 1) for various analyses and evaluations. Although not included in the illustrated example, in some embodiments, the analysis system can additionally store the original identifying data in one or more repositories. In at least one such embodiment, the analysis system stores the identifying data in a first repository (e.g., in the repository 110 of FIG. 1), and the de-identified data in a second, separate repository. This can allow the analysis system (or other systems) to use the de-identified data for a variety of purposes, without risking exposure of the identifying data.

At block 420, the analysis system (or other systems) can optionally evaluate, analyze, or otherwise process the de-identified data for a variety of purposes, as discussed above. For example, the analysis system may use the de-identified data to train machine learning models, to provide a device to the user (e.g., a CPAP mask or a VR headset), in the like. In embodiments, providing the device may include a variety of actions, including selecting a device from a set of alternatives (e.g., based on sizing), creating a device (e.g., a custom-fit mask), modifying an existing device (e.g., modifying an existing mask to better fit the user), and the like.

At block 425, the analysis system optionally initiates one or more actions based on this evaluation. For example, if the evaluation included selecting a device, the analysis system can proceed to indicate or suggest the device, to order the device or cause it to be shipped to the patient, and the like. In embodiments, a wide variety of actions can be initiated based on the de-identified data, depending on the particular implementation and deployment.

Example Method for De-Identifying, Linking, and Evaluating User Data

Figure 5:
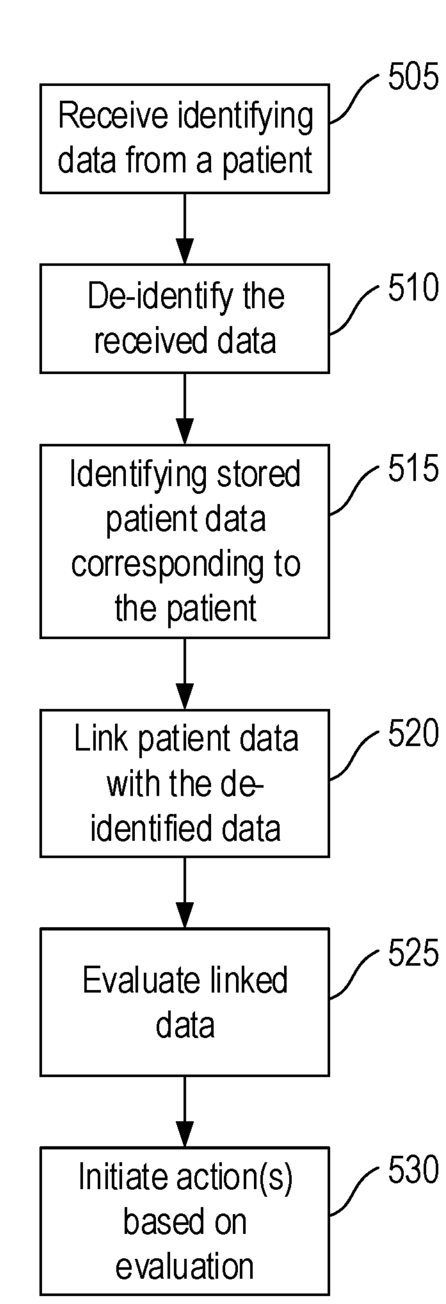
FIG. 5 is a flow diagram depicting an example method for de-identifying user data, linking the de-identified data from multiple sources, and evaluating the de-identified linked data.

FIG. 5 is a flow diagram depicting an example method for de-identifying user data, linking the de-identified data from multiple sources, and evaluating the de-identified linked data. In some embodiments, the method 500 is performed by an analysis system (e.g., analysis system 115 of FIGS. 1 and 2).

At block 505, the analysis system receives identifying data from a patient. For example, the identifying data may include face data of the user. As discussed above, this data is identifying in that it can uniquely identify the user (or identify a sufficiently small subset of users, such as when less than five or ten users "match" the face data). In some embodiments, the identifying data can include one or more images of the user's face, one or more three-dimensional meshes generated by scanning the user's face, and the like. In at least one embodiment, the received data can also include one or more other values, such as a name, birthdate, unique identifier, and the like for the patient.

At block 510, the analysis system de-identifies the received data. As discussed above, there may be a variety of de-identifying techniques that can be used, depending at least in part on the characteristics of the identifying data. For example, if the face data includes images of the user or a three-dimensional mesh of the user's face, the analysis system may extract one or more facial measurements from these images and/or mesh (e.g., a nose depth, nose width, face height, and the like) and/or landmark coordinates (e.g., three-dimensional coordinates of a set of points on the head, neck, ears, and/or face of the user). In some embodiments, if the identifying data includes a three-dimensional mesh, the analysis system can morph this mesh to a non-identifying form that preserves the principal measurements, shape, and/or structure of the user's face, while obscuring or removing identifying features. In some embodiments, the user-specific values or contributions for the principal components may be stored or maintained separately (e.g., in a separate repository or system) from the statistical model, enhancing privacy and security.

At block 515, the analysis system identifies (previously) stored patient data that corresponds to the patient. For example, the analysis system may use the patient's name, birthdate, identifier, and the like in order to find previously-stored records, corresponding to the patient, in one or more other repositories (e.g., repositories 210B and 210N in FIG. 2).

At block 520, the analysis system can then link the identified patient data (previously stored in one or more other repositories) with the newly de-identified patient data. For example, the analysis system may associate de-identified face data with other records indicating which medical device was recommended, which medical device was actually provided, whether the user has any issues or problems with the provided device, and the like.

At block 525, the analysis system can evaluate this linked data to perform a variety of operations. For example, as discussed above, the analysis system may determine whether the suggested device and provided device match, or whether the user has reported any issues with respect to the suggested and provided device (e.g., due to air leak around their nose). As discussed above, by performing the de-identification operation, these and other evaluations can be performed using data that would not otherwise be available for analysis, thereby improving the breadth of the analysis and yielding improved results of the operation.

At block 530, the analysis system can initiate one or more actions based on the evaluation. For example, if the analysis system determines that the suggested device and provided device do not align, the analysis system can generate one or more alerts or requests for information. These alerts may be transmitted to a variety of users, including the patient that received the device, the provider that selected or provided it, and the like.

As a further example, the analysis system may refine or reconfigure one or more systems, models, or other components as a result of the analysis. For example, if the analysis system determines that the user has experienced problems with a suggested and provided CPAP mask, the analysis system may determine that either the measurement system (e.g., the model(s) that extract facial measurements or coordinates from images or three-dimensional meshes) is faulty, and/or that the actual suggestions (based on a set of measurements or coordinates) are inaccurate. As a result, the analysis system can refine these models and systems, in order to ensure that future evaluations and suggestions are more accurate and reliable.

Example Method for Capturing De-Identified Face Data

Figure 6:
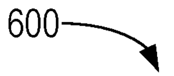
FIG. 6 is a flow diagram depicting an example method for capturing de-identified face data.
Figure 6:
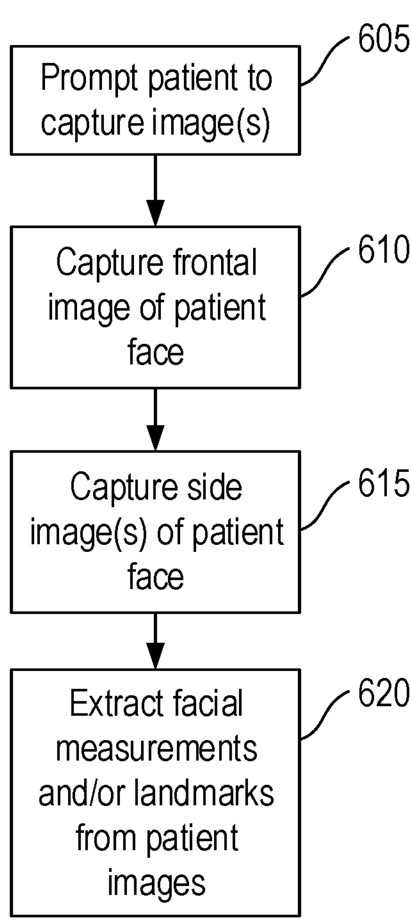

FIG. 6 is a flow diagram depicting an example method 600 for capturing de-identified face data. In some embodiments, the method 600 is performed by a user device (e.g., user device 105 of FIG. 1, and/or user device 205 of FIG. 2) and/or an analysis system (e.g., analysis system 115 of FIGS. 1 and 2). In at least one embodiment, the method 600 is implemented at least in part using the interface 305 of FIG. 3.

At block 605, a patient is prompted to capture one or more images of themselves for the purposes of determining facial measurements or other characteristics (e.g., landmark data). For example, a healthcare provider may transmit a link to the patient, asking them to follow the link to provide biographical or other survey data (e.g., indicating any sleep problems they currently experience), as well as facial measurements and/or landmarks.

At block 610, once the user accepts the prompt (e.g., selects a button to initiate the scan), the system captures one or more frontal images of the patient (e.g., using a webcam or other camera built in or otherwise coupled to the user device). In one embodiment, these frontal image(s) can be used to extract a variety of facial measurements, such as face height, nose and/or mouth width and height, and the like. In some embodiments, these images can similarly be used to extract or determine a variety of facial landmark coordinates, such as points on the nose, eyes, mouth, and the like.

At block 615, the analysis system can further capture one or more side or angled images of the patient's face. For example, the analysis system may instruct the user to turn their head from side to side, and selectively capture images (or selectively keep images, discarding others) where the user's head is angled at a defined angle to the side. In an embodiment, these side-facing images can be useful for extracting some measurements that are not readily visible in frontal images, such as the nose depth of the user. In some embodiments, these images can similarly be used to extract or determine a variety of facial landmark coordinates, such as points on the ears, chin, jaw, and the like.

At block 620, the system extracts one or more facial measurements and/or landmarks from the captured images. In embodiments, this extraction may be performed locally on the user device, and/or remotely by the analysis system. Generally, the particular measurements/landmarks that are extracted may differ depending on the particular implementation and deployment. For example, if the facial measurements or landmarks are to be used to suggest a device for the patient, the extracted measurements or landmarks may differ depending on the nature of the device (e.g., suggesting a CPAP machine may involve determining nose depth and width or nose coordinates, while suggesting a VR headset may involve determining the distance and/or landmark coordinates between the user's eyes or pupils).

In some embodiments, the captured images of the patient's face are transmitted to the analysis system for storage and/or analysis. Additionally, in some embodiments, the extracted measurements are also transmitted to the analysis system (or are determined locally by the analysis system). In this way, the measurements and/or images can be stored and used for a wide variety of analysis, evaluation, or other processing (e.g., to train machine learning models). Although the illustrated example describes using facial images to extract measurements and/or landmarks, the described techniques may similarly be used to extract facial measurements and/or landmarks from other data, such as 3D facial meshes, as discussed above.

Example Method for Extracting Facial Landmarks

Figure 7:
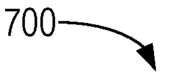
FIG. 7 is a flow diagram depicting an example method for extracting facial landmarks.
Figure 7:
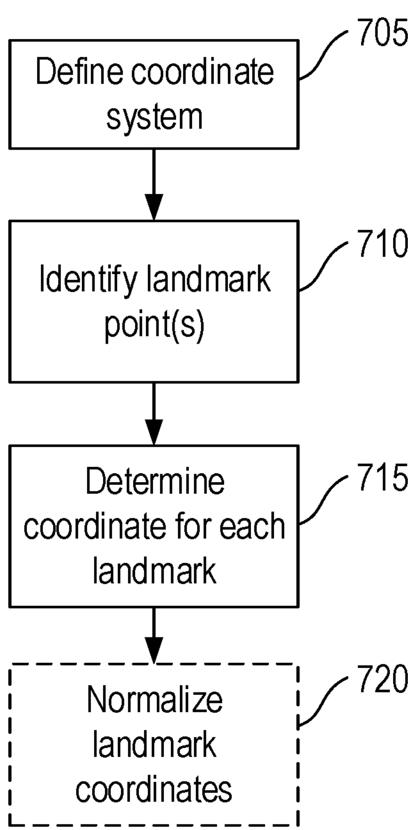

FIG. 7 is a flow diagram depicting an example method 700 for extracting facial landmarks. In some embodiments, the method 700 is performed by a user device (e.g., user device 105 of FIG. 1, and/or user device 205 of FIG. 2) and/or an analysis system (e.g., analysis system 115 of FIGS. 1 and 2). In at least one embodiment, the method 700 is implemented at least in part using the interface 305 of FIG. 3. In some embodiments, the method 700 provides additional detail for extracting facial landmarks in block 620 of FIG. 6. Although FIG. 6 generally discusses using facial images to extract facial landmarks, the method 700 may additionally or alternatively be performed using other data, such as 3D facial meshes.

At block 705, the system defines a coordinate system for the head or face of the user based on the accessed data (e.g., based on the image(s) and/or mesh(es)). In some embodiments, to define the coordinate system, the system can first identify a set of defined landmarks on the face or head of the user, and use these points to define the coordinate system. For example, in one embodiment, the system identifies the tragus point on each ear of the user, as well as the infraorbital point (e.g., corresponding to the infraorbital foramen) under each eye of the user using one or more models. In an embodiment, a first plane can be defined, intersecting these identified points or landmarks. Subsequently, a second plane can be defined perpendicular to the first and through the midplane of the user's face. Then, a third plane can be defined perpendicular to both the first and second planes. In this way, the intersection of the three planes can be used as a consistent origin for the coordinate system used to define the facial landmarks for the user.

At block 710, the system identifies one or more landmark points on the face, head, ears, and/or neck of the user. Generally, the specific points identified may vary depending on the particular implementation. In some embodiments, the landmark points can generally include one or more points on each ear, one or more points on the nose, one or more points on the mouth, and the like. In embodiments, the particular techniques used to identify the point(s) may vary depending on the particular implementation, and may include use of various techniques or operations such as machine learning models, image recognition models, fitting statistical shape models to the user's face, and the like.

At block 715, the system can determine or define, for each identified landmark, a corresponding coordinate based on the defined coordinate system. In this way, the landmark coordinates can be readily used to identify or determine a wide variety of data, such as measurements (e.g., distances between landmarks), angles between landmarks, and the like. In some embodiments, these landmarks may be considered non-identifying (even if they are quite dense), as they may not be sufficient to uniquely recognize or identify the user.

At block 720, the system can optionally normalize the landmark coordinates (e.g., to a defined range, such as between zero and one). In an aspect, the value or data used to normalize the coordinates may stored or maintained separately (e.g., in a separate repository or system) from the normalized coordinates themselves. In this way, even if an entity gains access to the normalized landmarks, they will be unable to reconstruct the original face without also knowing the normalizing value. That is, any attempt to reconstruct the face will fail to yield accurate measurements, as the scale will remain inaccurate.

In some embodiments, to normalize the coordinates, the system can divide each set of coordinates (e.g., each value in the coordinate triplet) by a normalization value, which may be defined in a number of ways. In some embodiments, the normalization value is defined based on the size of the original input image of the face. For example, the normalization value may be equal to the height or width of the image (in pixels). In some embodiments, other aspects, such as the face height or other facial measurements, may be used as the normalization value.

In this way, by storing the normalization value and the normalized coordinates separately, user privacy and security is enhanced (e.g., because one cannot determine the proper scale of the coordinates without also gaining access to the normalizing value).

Example Method for Use De-Identifying Three-Dimensional Face Meshes

Figure 8:
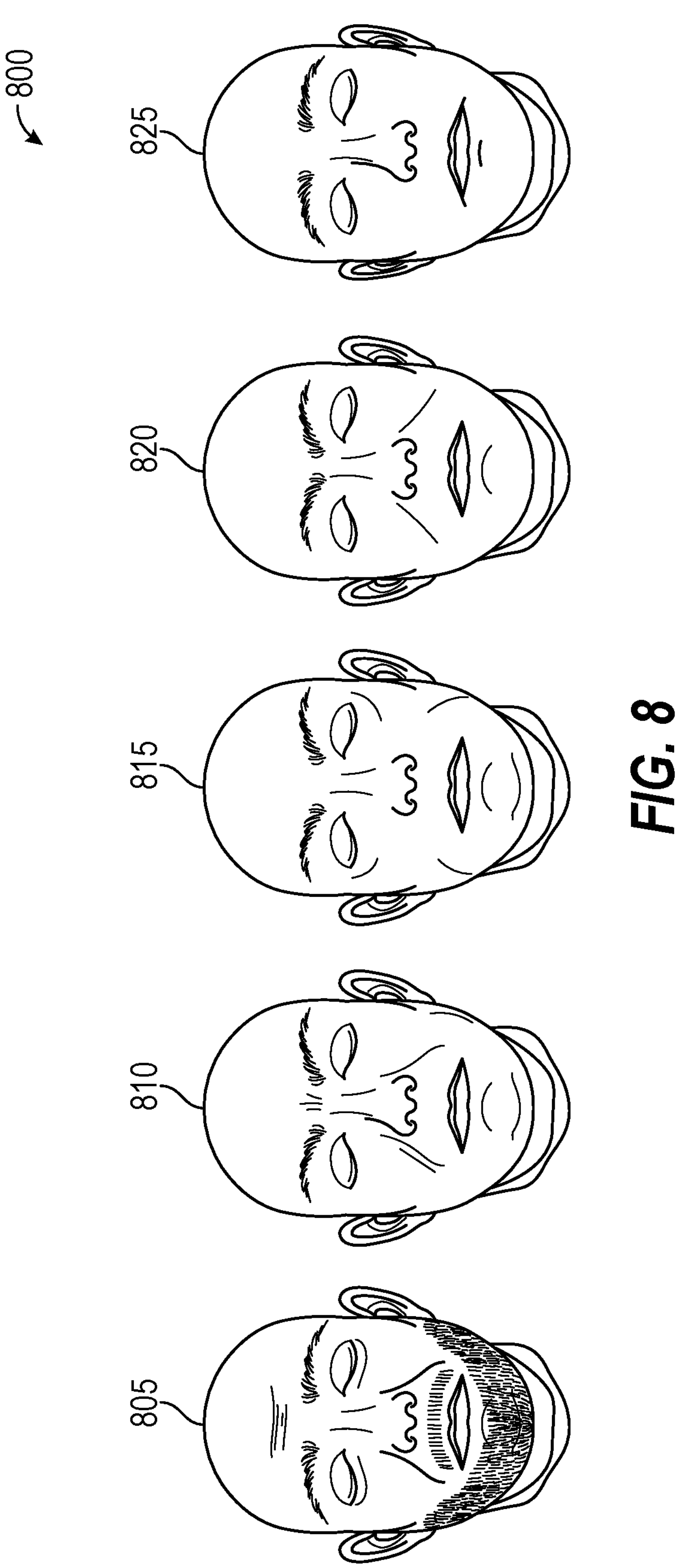
FIG. 8 depicts an example process of de-identifying three-dimensional face meshes.

FIG. 8 depicts an example process 800 of de-identifying three-dimensional face meshes. In some embodiments, the process 800 is performed by an analysis system (e.g., analysis system 115 of FIGS. 1 and 2).

In the illustrated embodiment, the process 800 involves iteratively morphing an identifiable mesh (e.g., collected using the interface 305 of FIG. 3) to a non-identifiable one. In one embodiment, the process 800 includes applying PCA and a set of one or more statistical models (e.g., representing average or common faces) to obfuscate or remove features that are highly-identifying, while preserving the overall face structure and shape. This can allow the three-dimensional mesh to be useful in various operations such as device recommendation (e.g., because the nose depth and shape remain similar), while preventing the patient from being identified (e.g., because other aspects such as facial hair, moles, and the like are generally smoothed or removed).

In the illustrated example, a first three-dimensional mesh 805 represents identifying face data for a patient or user. That is, the mesh 805 may correspond to an initial mesh generated by scanning the user's face (e.g., with a three-dimensional scanner or camera). As illustrated, this mesh 805 is readily identifiable, in that the patient who provided the face data is recognizable in the mesh.

As indicated by meshes 810, 815, and 820, the analysis system can apply an iterative morphing process to gradually remove identifying detail at each iteration, while retaining overall facial structure. Finally, as illustrated in mesh 825, the analysis system can output a de-identified facial mesh. As discussed above, this mesh 825 can generally retain the relevant structural features of the patient, while obfuscating or removing less relevant identifying features.

In embodiments, this de-identified mesh can then be used for a variety of applications, as discussed above, including device recommendation, training machine learning models, and the like.

In some embodiments, as discussed above, the morphing process 800 results in generation of a set of values (e.g., weights or contributions for principal components) which are specific to the user depicted by the mesh 805. Using these values, the statistical face model may be used to reconstruct the original mesh 805. In an embodiment, therefore, the set of values is stored or maintained separately from the statistical face model(s) (e.g., in a separate repository or computing system). This ensures that any entity having access to one repository still cannot reconstruct user faces without also accessing the other.

Example Method for Evaluating Linked Data to Initiate Remedial Actions

Figure 9:
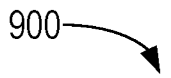
FIG. 9 is a flow diagram depicting an example method for evaluating linked data to initiate remedial actions.
Figure 9:
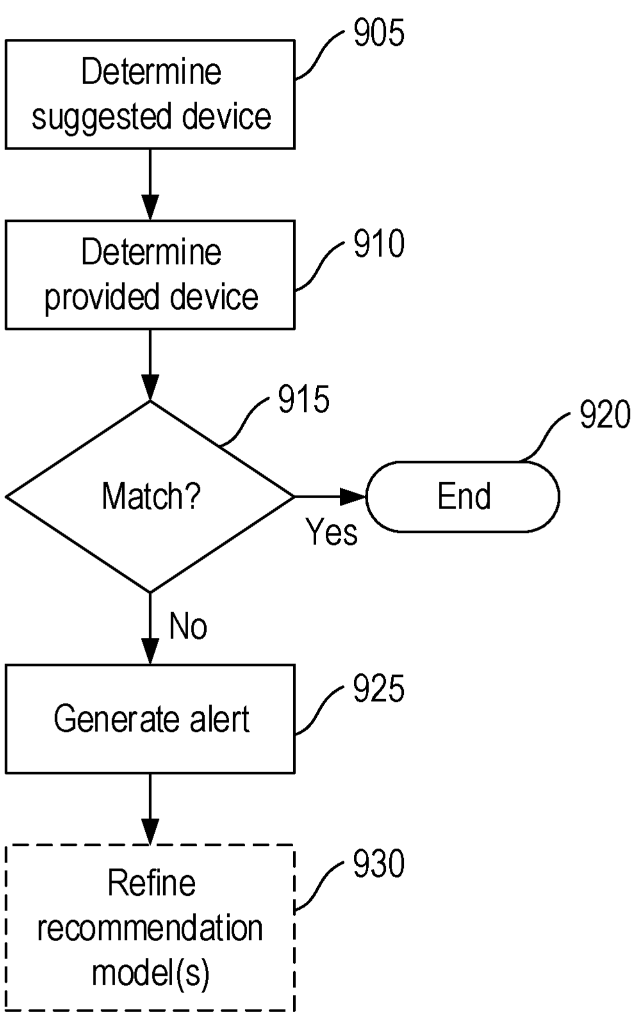

FIG. 9 is a flow diagram depicting an example method 900 for evaluating linked data to initiate remedial actions. In some embodiments, the method 900 is performed by an analysis system (e.g., analysis system 115 of FIGS. 1 and 2).

In at least one embodiment, the method 900 is performed using linked or associated data from multiple repositories. For example, the method 900 may be performed using the merged de-identified data 225 of FIG. 2, and/or the linked data generated in block 520 of FIG. 5. Generally, this linked data can include one or more elements that have undergone a de-identification process, as discussed above.

At block 905, the analysis system determines a suggested device for a given user, based on the linked data. For example, from a mask selection component or data store, the analysis system can determine which CPAP mask was recommended for the user (e.g., using a recommendation model, based on a set of facial measurements and/or facial landmarks of the user).

At block 910, the analysis system can also determine a device that was actually provided to the user, based on this linked data. For example, from an equipment data store, the analysis system can determine which device(s) have been provided, when they were provided, whether any resupplies are due, and the like. In some embodiments, determining the provided device can include determining which device was most-recently provided, determining which was provided at the time the suggestion was made, and the like.

At block 915, the analysis system can then determine whether the suggested device and the provided device match. That is, the analysis system can determine whether the user was actually provided a device that aligns with the suggested or recommended device. For example, if the suggested device is a particular model and size, the analysis system can determine whether the provided mask is the same model, the same size, or both.

If, at block 915, the analysis system determines that the suggested and provided devices match, the method 900 can terminate at block 920. That is, the analysis system can determine that no further action is needed, because the recommendation was followed (which may indicate that the recommendation model is accurate and/or trusted).

If, at block 915, the analysis system determines that the suggested and provided devices do not match, the method 900 continues to block 925. In some embodiments, the analysis system determines that this misalignment exists if, in response to the suggestion, a different device was provided (e.g., if the provider ignored the suggestion).

In some embodiments, the analysis system determines that misalignment exists if the currently-provided mask does not match the suggested one (even if a different mask was originally provided at the time the suggestion was generated). That is, suppose the provider originally provided the suggested mask (e.g., listening to the recommendation model). If the patient subsequently had issues that caused them to try a different mask (the newly-provided one), the analysis system may infer that the recommendation model is not operating with sufficient accuracy.

At block 925, the analysis system generates one or more alerts based on the misalignment. In at least one embodiment, these alerts can be provided to one or more entities, depending at least in part on the nature of the misalignment. For example, if the analysis system determines that the provider ignored the suggestion, it may prompt the provider to indicate why the suggestion was ignored, and/or notify the user that they are using a different mask than what was recommended. If the analysis system determines that the provider followed the suggestion but that the user later received a different device, the analysis system can prompt the provider and/or user to inquire as to why the new device was requested and/or provided.

At block 930, the analysis system optionally performs remedial actions, such as by refining the device recommendation model(s) based on the misalignment. That is, the analysis system can refine one or more parameters, rules, weights, or other elements of the recommendation model (used to generate the suggested device) in order to improve its future recommendations. For example, if the recommendation model is a machine learning-based model, the analysis system can refine the internal weights and parameters of the model. In some embodiments, the remedial techniques can include selecting or suggesting a preferred measurement technique for future recommendations (e.g., determining to use morphed 3D meshes rather than images, because the 3D meshes result in more accurate suggestions).

Example Method for De-Identifying and Linking Patient Data

Figure 10:
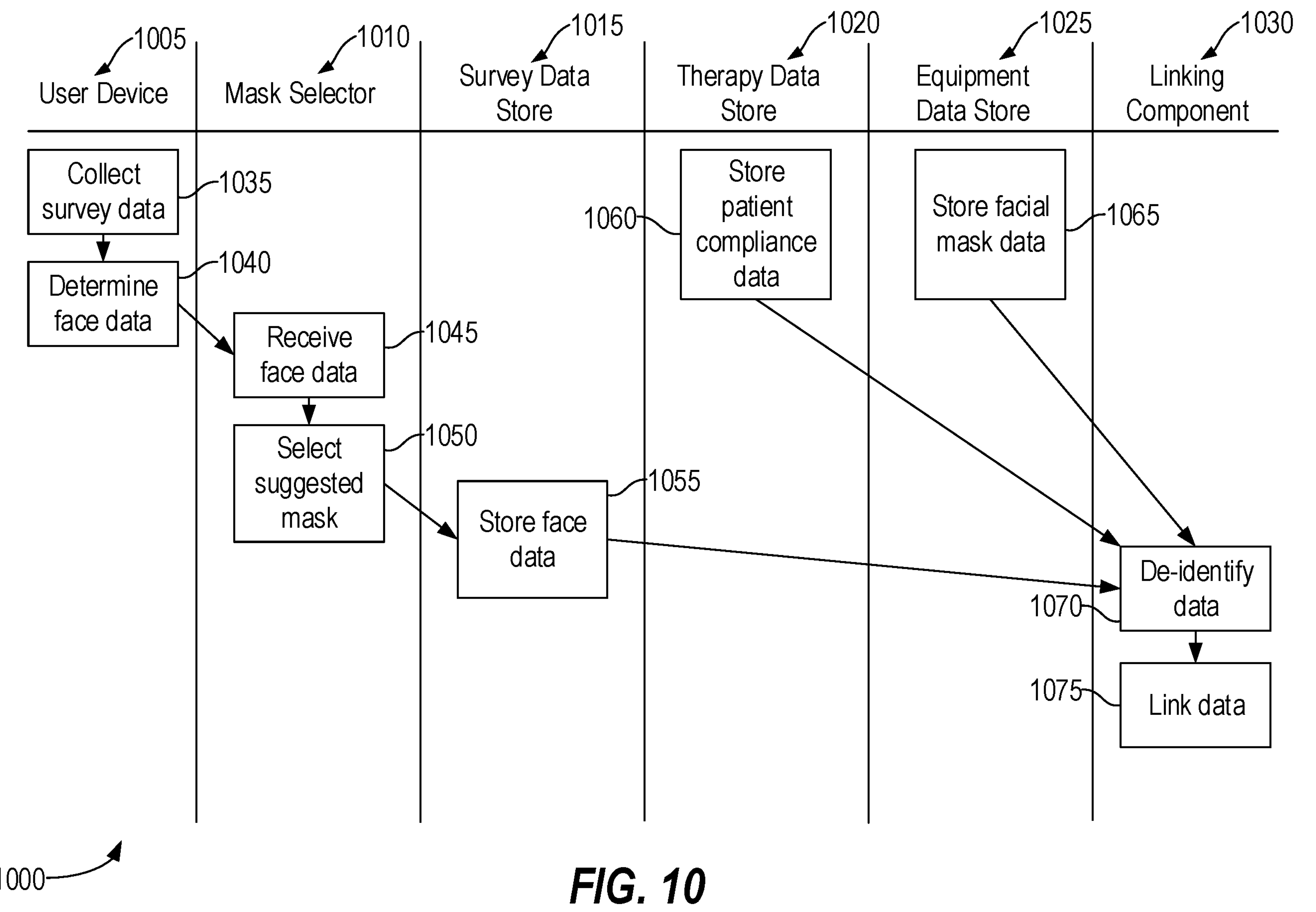
FIG. 10 is a flow diagram depicting an example method for de-identifying and linking patient data.

FIG. 10 is a flow diagram depicting an example method 1000 for de-identifying and linking patient data.

The illustrated example depicts a method 1000 performed across a number of components, including a user device 1005, a mask selector 1010, a survey data store 1015, a therapy data store 1020, an equipment data store 1025, and a linking component 1030. In embodiments, however, the operations and functionality of the method 1000 may be combined or distributed across any number and arrangement of components.

In at least one embodiment, the mask selector 1010, survey data store 1015, therapy data store 1020, equipment data store 1025, and linking component 1030 may each be part of an analysis system, such as the analysis system 115 of FIGS. 1 and 2.

At block 1035, the user device 1005 collects survey data from the user. For example, in response to a prompt from the analysis system or a healthcare provider, the user may provide information such as their name, birthdate, sleeping patterns, and the like. At block 1040, the user device 1005 also determines face data for the user. As discussed above, this may include capturing one or more images of the user, generating a three-dimensional mesh of the user's face, and the like. In at least one embodiment, this face data is identifying.

At block 1045, the mask selector 1010 receives the generated face data for the user. At block 1050, the mask selector 1010 can then select a suggested mask based on the face data. For example, using one or more machine learning models, rules-based models, or other techniques, the mask selector 1010 can generally evaluate the face data to select (or otherwise design or provide) a facial mask that should fit the user's face. Although facial masks are used in this example, as discussed above, the system may additionally or alternatively suggest other devices, such as VR headsets, based on the face data. Though the illustrated example depicts the mask selector 1010 selecting the suggested mask based on the face data, in some embodiments, the mask selector 1010 (or another component) can select the mask based on de-identified face data, as discussed above.

At block 1055, the survey data store 1015 stores the face data. In at least one embodiment, the survey data store 1015 also stores the survey data and/or the suggested mask for the user. Further, at block 1060 and 1065, the therapy data store 1020 and equipment data store 1025 store patient compliance data and facial mask data, respectively.

In an embodiment, as discussed above, the patient compliance data can generally indicate whether the user is using the provided device, how often they user it, whether they have indicated any complaints or problems with the device, and the like. The facial mask data can generally indicate which mask(s) have been provided to the user, when they were provided, which mask(s) the user currently uses, and the like.

At block 1070, the linking component 1030 can receive and de-identify the face data, patient compliance data, and/or facial mask data. For example, as discussed above, the linking component 1030 may de-identify the face data such that the de-identified data does not uniquely identify the user (e.g., by extracting one or more measurements or landmarks, morphing a three-dimensional mesh, and the like). In some embodiments, as discussed above, the linking component 1030 (or another component) can de-identify the face data prior to selecting the suggested mask. This de-identified data can then be used to select the suggested mask. That is, block 1070 may be performed prior to blocks 1045 and/or 1050. For example, the user device 1005 may perform block 1070, and transmit de-identified face data to the mask selector 1010. Alternatively, the mask selector 1010 may perform block 1070 prior to block 1050.

Further, at block 1075, the linking component can link this de-identified data, as discussed above. This merged and de-identified data can thereafter be used for a wide variety of operations, including evaluating the efficacy of the mask selector (and potentially refining its performance), training other models, and the like.

Example Method for De-Identifying and Associating Patient Data

Figure 11:
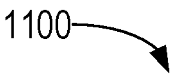
FIG. 11 is a flow diagram depicting an example method for de-identifying and associating patient data.
Figure 11:
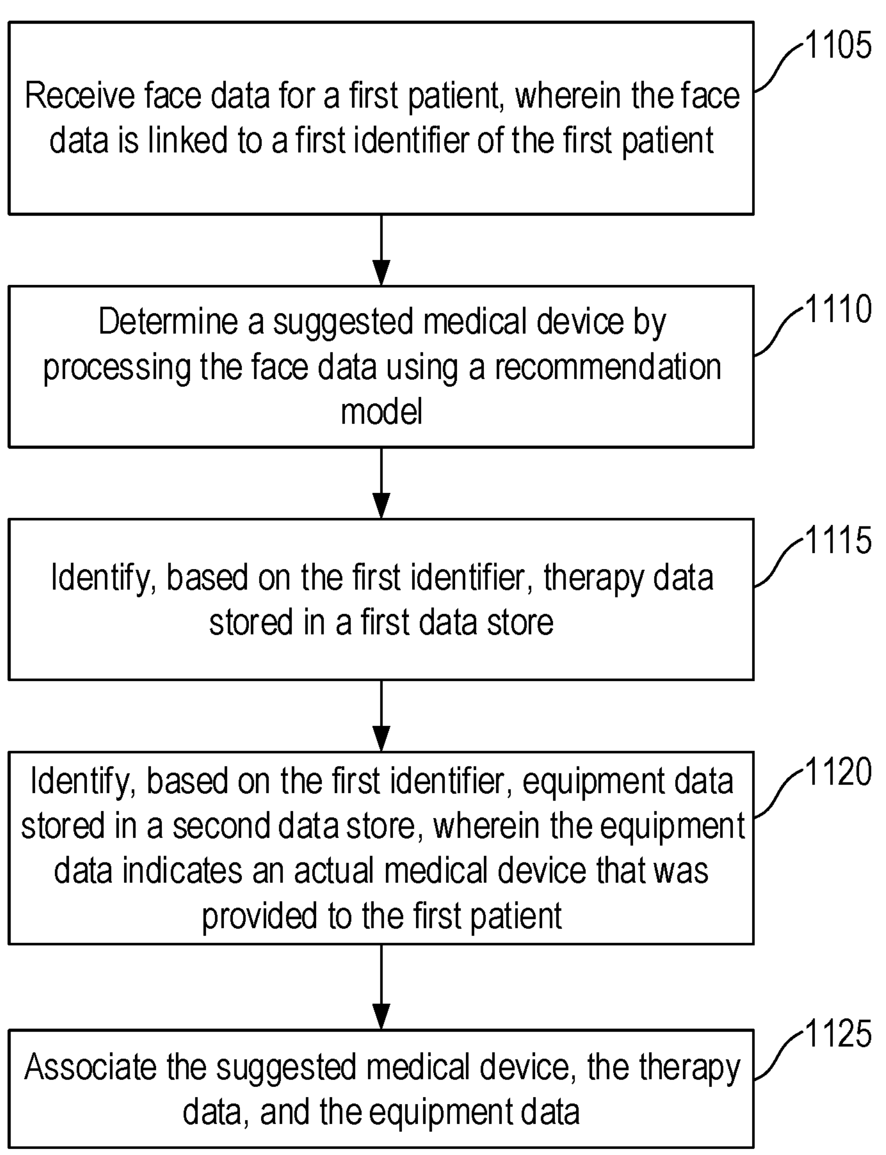

FIG. 11 is a flow diagram depicting an example method 1100 for de-identifying and associating patient data. In some embodiments, the method 1100 is performed by an analysis system (e.g., analysis system 115 of FIGS. 1 and 2).

At block 1105, face data is received for a first patient, wherein the face data is linked to a first identifier of the first patient.

At block 1110, a suggested medical device is determined by processing the face data using a recommendation model.

At block 1115, therapy data stored in a first data store is identified based on the first identifier.

At block 1120, equipment data stored in a second data store is identified based on the first identifier, wherein the equipment data indicates an actual medical device that was provided to the first patient.

At block 1125, the suggested medical device, the therapy data, and the equipment data are associated.

In some embodiments, the face data comprises one or more facial measurements of the first patient, and wherein the face data does not uniquely identify the first patient, and the method 1100 further comprises associating the face data with the suggested medical device, therapy data, and equipment data.

In some embodiments, the method 1100 further includes determining a set of coordinates for a set of facial landmarks based on the face data and normalizing the set of coordinates using a normalization value.

In some embodiments, the face data comprises a three-dimensional (3D) mesh of a face of the first patient, and the method 1100 further comprises de-identifying the face data prior to identifying the therapy data or the equipment data.

In some embodiments, de-identifying the face data comprises extracting one or more facial measurements based on the 3D mesh, the one or more facial measurements do not uniquely identify the first patient, and the method 1100 further comprises associating the one or more facial measurements with the suggested medical device, therapy data, and equipment data, wherein the face data is not linked to the therapy data or equipment data.

In some embodiments, de-identifying the face data comprises generating a morphed 3D mesh based on the 3D mesh, wherein the morphed 3D mesh does not uniquely identify the first patient, and the method 1100 further comprises associating the morphed 3D mesh with the suggested medical device, therapy data, and equipment data, wherein the face data is not linked to the therapy data or equipment data.

In some embodiments, generating the morphed 3D mesh comprises morphing the 3D mesh based on principal component analysis (PCA) and a set of statistical shape models for human faces.

In some embodiments, the method 1100 further includes outputting, via a graphical user interface (GUI), the associated suggested medical device, therapy data, and equipment data.

In some embodiments, the method 1100 further includes determining, based on the associated suggested medical device and equipment data, that the suggested medical device and actual medical device do not match, and generating an alert indicating that the suggested medical device and the actual medical device do not match.

In some embodiments, the method 1100 further includes transmitting, to a provider that provided the actual medical device, a request for information relating to why the actual medical device was provided.

In some embodiments, the method 1100 further includes transmitting, to the first patient, an indication that the actual medical device does not match the suggested medical device.

In some embodiments, the method 1100 further includes determining, based on the associated therapy data and equipment data, that the first patient has one or more issues with the actual medical device, and refining the recommendation model based on the one or more issues.

In some embodiments, the method 1100 further includes selecting a first measurement technique, of a plurality of measurement techniques, for generating face data based at least in part on the associated suggested medical device, the therapy data, and the equipment data.

In some embodiments, the face data was received in response to transmitting, to the first patient, a request to provide the face data.

In some embodiments, the suggested medical device is a continuous positive airway pressure (CPAP) mask.

Example Method for Collecting De-Identified Data

Figure 12:
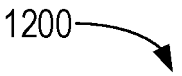
FIG. 12 is a flow diagram depicting an example method for collecting de-identified data for analysis.
Figure 12:
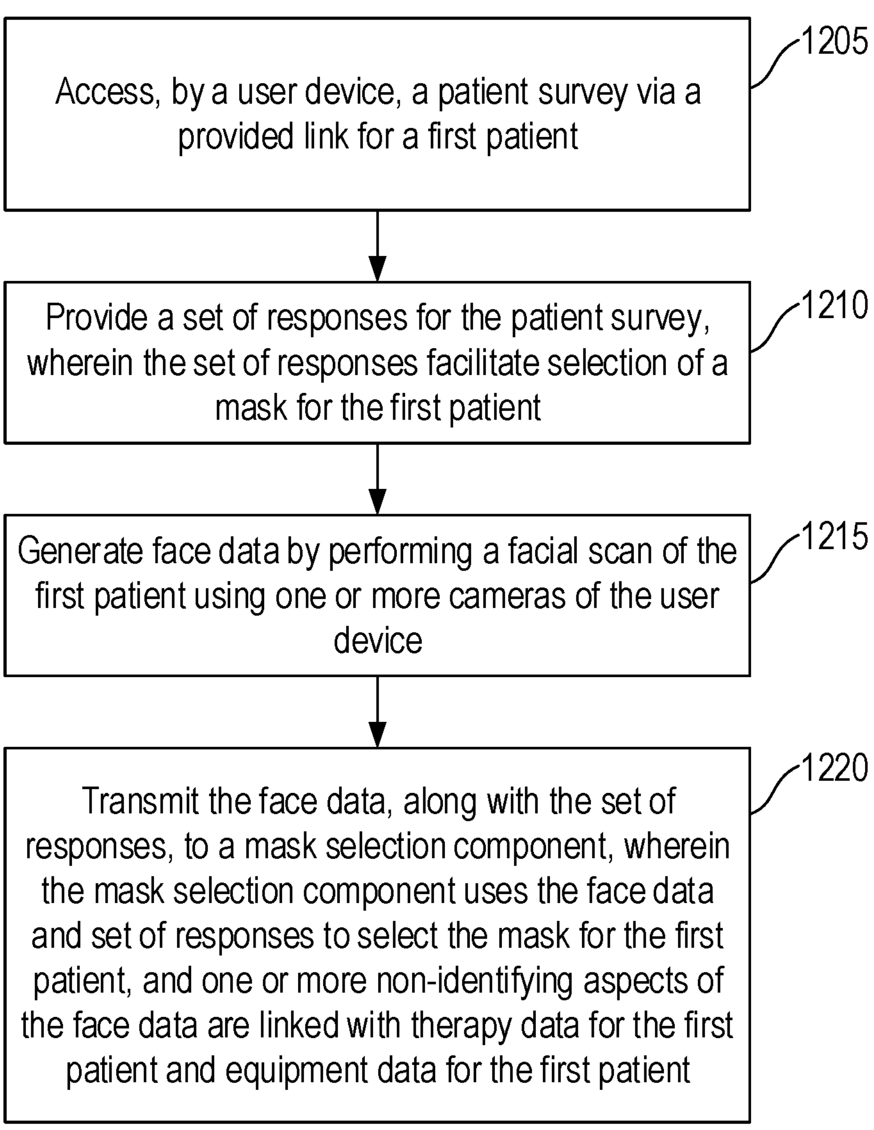

FIG. 12 is a flow diagram depicting an example method 1200 for collecting de-identified data for analysis. In some embodiments, the method 1200 is performed by a user device (e.g., user device 105 of FIG. 1 or user device 205 of FIG. 2).

At block 1205, a patient survey is accessed, by a user device, via a provided link for a first patient.

At block 1210, a set of responses are provided for the patient survey, wherein the set of responses facilitate selection of a mask for the first patient.

At block 1215, face data is generated by performing a facial scan of the first patient using one or more cameras of the user device.

At block 1220, the face data, along with the set of responses, is transmitted to a mask selection component, wherein the mask selection component uses the face data and set of responses to select the mask for the first patient, and one or more non-identifying aspects of the face data are linked with therapy data for the first patient and equipment data for the first patient.

In some embodiments, the face data comprises one or more facial measurements of the first patient that do not uniquely identify the first patient, the one or more facial measurements are generated by the user device by processing one or more images, captured by the one or more cameras of the user device, using one or more machine learning models, and the one or more images are not transmitted to the mask selection component.

In some embodiments, the method 1200 further includes determining a set of coordinates for a set of facial landmarks based on the face data and normalizing the set of coordinates using a normalization value.

In some embodiments, the face data comprises a three-dimensional (3D) mesh of a face of the first patient, and prior to linking the one or more non-identifying aspects of the face data with the therapy data and the equipment data, the face data is de-identified.

In some embodiments, de-identifying the face data comprises extracting one or more facial measurements based on the 3D mesh, and the one or more non-identifying aspects of the face data correspond to the one or more facial measurements.

In some embodiments, de-identifying the face data comprises generating a morphed 3D mesh based on the 3D mesh, and the one or more non-identifying aspects of the face data correspond to the morphed 3D mesh.

Example Method for Determining Medical Devices Using De-Identified Data

Figure 13:
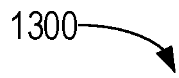
FIG. 13 is a flow diagram depicting an example method for determining medical devices using de-identified data.
Figure 13:
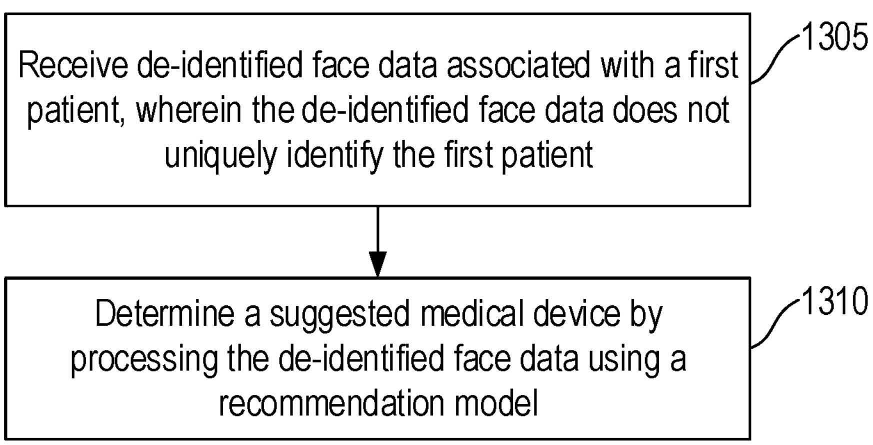

FIG. 13 is a flow diagram depicting an example method 1300 for determining medical devices using de-identified data. In some embodiments, the method 1300 is performed by an analysis system (e.g., analysis system 115 of FIGS. 1 and 2).

At block 1305, de-identified face data associated with a first patient is received, wherein the de-identified face data does not uniquely identify the first patient.

At block 1310, a suggested medical device is determined by processing the de-identified face data using a recommendation model.

In some embodiments, the de-identified face data comprises at least one of: one or more facial measurements that were extracted from one or more images of a face of the first patient, or one or more facial landmark coordinates that were extracted from one or more images of a face of the first patient and were normalized using a normalization value.

In some embodiments, the de-identified face data was generated by extracting one or more facial measurements based on a three-dimensional (3D) mesh of a face of the first patient.

In some embodiments, the de-identified face data was generated by generating a morphed three-dimensional (3D) mesh based on a 3D mesh of a face of the first patient, wherein the morphed 3D mesh does not uniquely identify the first patient.

In some embodiments, generating the morphed 3D mesh comprises morphing the 3D mesh based on principal component analysis (PCA) and a set of statistical shape models for human faces.

In some embodiments, the method 1300 further includes outputting, via a graphical user interface (GUI), the suggested medical device.

In some embodiments, determining the suggested medical device comprises determining a set of measurement ranges that the suggested medical device is designed to fit, and selecting the suggested medical device, based on the de-identified face data and the set of measurement ranges.

In some embodiments, determining the suggested medical device comprises identifying a set of modifications for a first medical device, based on the de-identified face data suggesting the first medical device, and suggesting along the set of modifications.

In some embodiments, the suggested medical device is a continuous positive airway pressure (CPAP) mask.

Example Client-Server System for Linking De-Identified Data

Figure 14:
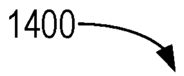
FIG. 14 is a flow diagram depicting an example method for linking de-identified data.
Figure 14:
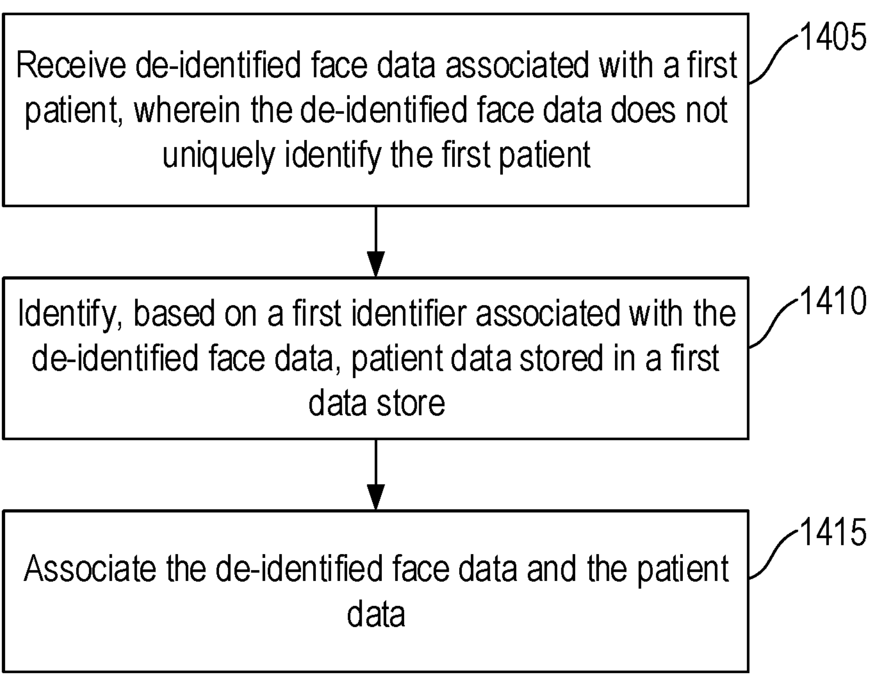

FIG. 14 is a flow diagram depicting an example method 1400 for linking de-identified data. In some embodiments, the method 1400 is performed by an analysis system (e.g., analysis system 115 of FIGS. 1 and 2).

At block 1405, de-identified face data associated with a first patient is received, wherein the de-identified face data does not uniquely identify the first patient.

At block 1410, patient data stored in a first data store is identified based on a first identifier associated with the de-identified face data.

At block 1415, the de-identified face data and the patient data are associated.

In some embodiments, the patient data corresponds to therapy data for the first patient, wherein the therapy data indicates patient compliance with one or more prescribed therapies.

In some embodiments, the method 1400 further includes determining, based on the therapy data, that the first patient has one or more issues with a prescribed medical device, and identifying a suggested medical device based on the de-identified face data.

In some embodiments, the patient data corresponds to equipment data for the first patient, wherein the equipment data indicates an actual medical device that was provided to the first patient.

In some embodiments, the method 1400 further includes determining, based on the equipment data, that the actual medical device does not match a suggested medical device for the first patient, and generating an alert indicating that the suggested medical device and the actual medical device do not match.

In some embodiments, the method 1400 further includes transmitting, to a provider that provided the actual medical device, a request for information relating to why the actual medical device was provided.

In some embodiments, the method 1400 further includes transmitting, to the first patient, an indication that the actual medical device does not match the suggested medical device.

Figure 15:
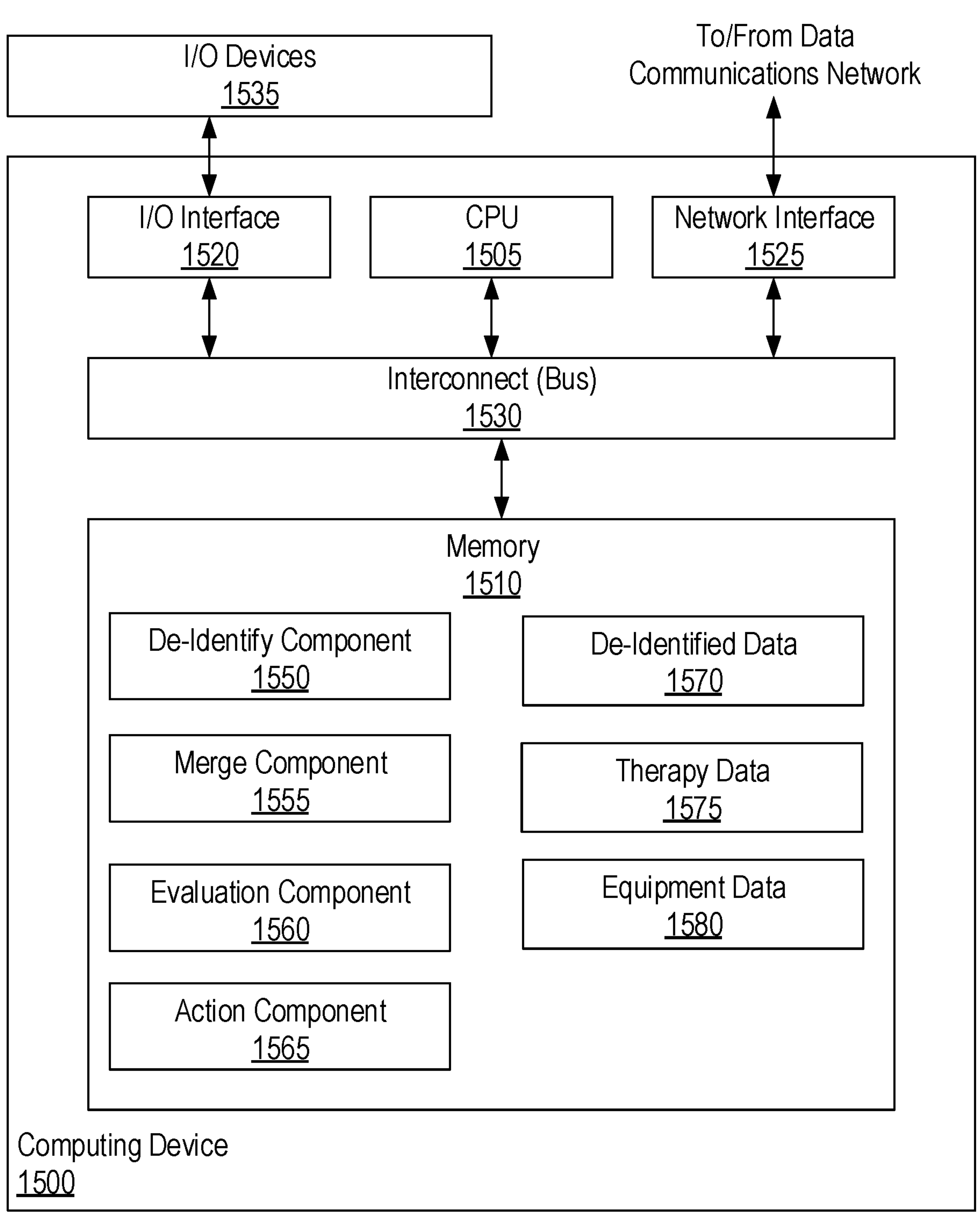
FIG. 15 depicts an example computing device configured to perform various aspects of the present disclosure.

Example Processing System for De-Identifying, Linking, and Evaluating User Data FIG. 15 depicts an example computing device 1500 configured to perform various aspects of the present disclosure. Although depicted as a physical device, in embodiments, the computing device 1500 may be implemented using virtual device(s), and/or across a number of devices (e.g., in a cloud environment). In one embodiment, the computing device 1500 corresponds to or implements the analysis system 115 of FIGS. 1 and 2.

As illustrated, the computing device 1500 includes a CPU 1505, memory 1510, a network interface 1525, and one or more I/O interfaces 1520. Though not included in the depicted example, in some embodiments, the computing device 1500 also includes one or more storages. In the illustrated embodiment, the CPU 1505 retrieves and executes programming instructions stored in memory 1510, as well as stores and retrieves application data residing in memory 1510 and/or storage (not depicted). The CPU 1505 is generally representative of a single CPU and/or GPU, multiple CPUs and/or GPUs, a single CPU and/or GPU having multiple processing cores, and the like. The memory 1510 is generally included to be representative of a random access memory. In an embodiment, if storage is present, it may include any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 1535 (such as keyboards, monitors, etc.) are connected via the I/O interface(s) 1520. Further, via the network interface 1525, the computing device 1500 can be communicatively coupled with one or more other devices and components (e.g., via a network, which may include the Internet, local network(s), and the like). As illustrated, the CPU 1505, memory 1510, network interface(s) 1525, and I/O interface(s) 1520 are communicatively coupled by one or more buses 1530.

In the illustrated embodiment, the memory 1510 includes a de-identify component 1550, a merge component 1555, an evaluation component 1560, and an action component 1565, which may perform one or more embodiments discussed above. Although depicted as discrete components for conceptual clarity, in embodiments, the operations of the depicted components (and others not illustrated) may be combined or distributed across any number of components. Further, although depicted as software residing in memory 1510, in embodiments, the operations of the depicted components (and others not illustrated) may be implemented using hardware, software, or a combination of hardware and software.

For example, the de-identify component 1550 may generally be used to de-identify facial data from users (e.g., to extract facial measurements from images or meshes, and/or to morph meshes into non-identifying forms). The merge component 1555 may be used to link or merge data (e.g., de-identified face data, as well as survey data, therapy data, and/or equipment data) from multiple different repositories to enable more dynamic evaluation. The evaluation component 1560 may perform these analyses on the de-identified and/or merged data, as discussed above. The action component 1565 may generally trigger, initiate, or otherwise facilitate any desired actions (such as transmitting alerts, refining machine learning models, and the like).

In the illustrated example, the memory 1510 further includes de-identified data 1570, therapy data 1575, and equipment data 1580. Although depicted as residing in memory 1510, the de-identified data 1570, therapy data 1575, and equipment data 1580 may be stored in any suitable location. In at least one embodiment, as discussed above, the de-identified data 1570, therapy data 1575, and equipment data 1580 may be stored in separate repositories. Generally, the de-identified data 1570 includes de-identified face data for one or more users. Therapy data 1575 may include compliance data (e.g., indicating whether the user(s) are using the supplied equipment), and equipment data 1580 may indicate what equipment has been provided to each user.

Example Clauses

Clause 1: A method, comprising: receiving face data for a first patient, wherein the face data is linked to a first identifier of the first patient; determining a suggested medical device by processing the face data using a recommendation model; identifying, based on the first identifier, therapy data stored in a first data store; identifying, based on the first identifier, equipment data stored in a second data store, wherein the equipment data indicates an actual medical device that was provided to the first patient; and associating the suggested medical device, the therapy data, and the equipment data.

Clause 2: The method of Clause 1, wherein: the face data comprises one or more facial measurements of the first patient, and wherein the face data does not uniquely identify the first patient, and the method further comprises associating the face data with the suggested medical device, therapy data, and equipment data.

Clause 3: The method of any one of Clauses 1-2, the method further comprising: determining a set of coordinates for a set of facial landmarks based on the face data; and normalizing the set of coordinates using a normalization value.

Clause 4: The method of any one of Clauses 1-3, wherein: the face data comprises a three-dimensional (3D) mesh of a face of the first patient, and the method further comprises de-identifying the face data prior to identifying the therapy data or the equipment data.

Clause 5: The method of any one of Clauses 1-4, wherein: de-identifying the face data comprises extracting one or more facial measurements based on the 3D mesh, the one or more facial measurements do not uniquely identify the first patient, and the method further comprises: associating the one or more facial measurements with the suggested medical device, therapy data, and equipment data, wherein the face data is not linked to the therapy data or equipment data.

Clause 6: The method of any one of Clauses 1-5, wherein: de-identifying the face data comprises generating a morphed 3D mesh based on the 3D mesh, wherein the morphed 3D mesh does not uniquely identify the first patient, and the method further comprises: associating the morphed 3D mesh with the suggested medical device, therapy data, and equipment data, wherein the face data is not linked to the therapy data or equipment data.

Clause 7: The method of any one of Clauses 1-6, wherein generating the morphed 3D mesh comprises morphing the 3D mesh based on principal component analysis (PCA) and a set of statistical shape models for human faces.

Clause 8: The method of any one of Clauses 1-7, further comprising outputting, via a graphical user interface (GUI), the associated suggested medical device, therapy data, and equipment data.

Clause 9: The method of any one of Clauses 1-8, further comprising: determining, based on the associated suggested medical device and equipment data, that the suggested medical device and actual medical device do not match; and generating an alert indicating that the suggested medical device and the actual medical device do not match.

Clause 10: The method of any one of Clauses 1-9, further comprising: transmitting, to a provider that provided the actual medical device, a request for information relating to why the actual medical device was provided.

Clause 11: The method of any one of Clauses 1-10, further comprising: transmitting, to the first patient, an indication that the actual medical device does not match the suggested medical device.

Clause 12: The method of any one of Clauses 1-11, further comprising: determining, based on the associated therapy data and equipment data, that the first patient has one or more issues with the actual medical device, and refining the recommendation model based on the one or more issues.

Clause 13: The method of any one of Clauses 1-12, further comprising: selecting a first measurement technique, of a plurality of measurement techniques, for generating face data based at least in part on the associated suggested medical device, the therapy data, and the equipment data.

Clause 14: The method of any one of Clauses 1-13, wherein the face data was received in response to transmitting, to the first patient, a request to provide the face data.

Clause 15: The method of any one of Clauses 1-14, wherein the suggested medical device is a continuous positive airway pressure (CPAP) mask.

Clause 16: A method, comprising: accessing, by a user device, a patient survey via a provided link for a first patient; providing a set of responses for the patient survey, wherein the set of responses facilitate selection of a mask for the first patient; generating face data by performing a facial scan of the first patient using one or more cameras of the user device; transmitting the face data, along with the set of responses, to a mask selection component, wherein: the mask selection component uses the face data and set of responses to select the mask for the first patient; and one or more non-identifying aspects of the face data are linked with therapy data for the first patient and equipment data for the first patient.

Clause 17: The method of Clause 16, wherein: the face data comprises one or more facial measurements of the first patient that do not uniquely identify the first patient, the one or more facial measurements are generated by the user device by processing one or more images, captured by the one or more cameras of the user device, using one or more machine learning models, and the one or more images are not transmitted to the mask selection component.

Clause 18: The method of any one of Clauses 16-17, The method of claim 16, the method further comprising: determining a set of coordinates for a set of facial landmarks based on the face data; and normalizing the set of coordinates using a normalization value.

Clause 19: The method of any one of Clauses 16-18, wherein: the face data comprises a three-dimensional (3D) mesh of a face of the first patient, and prior to linking the one or more non-identifying aspects of the face data with the therapy data and the equipment data, the face data is de-identified.

Clause 20: The method of any one of Clauses 16-19, wherein: de-identifying the face data comprises extracting one or more facial measurements based on the 3D mesh, and the one or more non-identifying aspects of the face data correspond to the one or more facial measurements.

Clause 21: The method of any one of Clauses 16-20, wherein: de-identifying the face data comprises generating a morphed 3D mesh based on the 3D mesh, and the one or more non-identifying aspects of the face data correspond to the morphed 3D mesh.

Clause 22: A system, comprising: a user device configured to perform an operation comprising: collecting, from a first patient, survey data; and determining, using on one or more imaging devices, face data for the first patient; a mask selector component configured to perform an operation comprising: receiving the face data for the first patient; and selecting a suggested facial mask based on the face data; a first data store configured to store the survey data and the face data for the first patient; a second data store configured to store therapy data for the first patient, wherein the therapy data indicates patient compliance with one or more prescribed therapies; a third data store configured to store equipment data for the first patient, wherein the equipment data indicates an actual facial mask provided to the first patient; and a linking component configured to perform an operation comprising: de-identifying the face data, such that the face data does not uniquely identify the first patient; and linking the de-identified face data, the therapy data, and the equipment data.

Clause 23: A method, comprising: receiving de-identified face data associated with a first patient, wherein the de-identified face data does not uniquely identify the first patient; and determining a suggested medical device by processing the de-identified face data using a recommendation model.

Clause 24: The method of Clause 23, wherein the de-identified face data comprises at least one of: one or more facial measurements that were extracted from one or more images of a face of the first patient, or one or more facial landmark coordinates that were extracted from one or more images of a face of the first patient and were normalized using a normalization value.

Clause 25: The method of any one of Clauses 23-24, wherein: the de-identified face data was generated by extracting one or more facial measurements based on a three-dimensional (3D) mesh of a face of the first patient.

Clause 26: The method of any one of Clauses 23-25, wherein: the de-identified face data was generated by generating a morphed three-dimensional (3D) mesh based on a 3D mesh of a face of the first patient, wherein the morphed 3D mesh does not uniquely identify the first patient.

Clause 27: The method of any one of Clauses 23-26, wherein generating the morphed 3D mesh comprises morphing the 3D mesh based on principal component analysis (PCA) and a set of statistical shape models for human faces.

Clause 28: The method of any one of Clauses 23-27, further comprising: outputting, via a graphical user interface (GUI), the suggested medical device.

Clause 29: The method of any one of Clauses 23-28, wherein determining the suggested medical device comprises: determining a set of measurement ranges that the suggested medical device is designed to fit; and selecting the suggested medical device, based on the de-identified face data and the set of measurement ranges.

Clause 30: The method of any one of Clauses 23-29, wherein determining the suggested medical device comprises: identifying a set of modifications for a first medical device, based on the de-identified face data; and suggesting the first medical device; and suggesting along the set of modifications.

Clause 31: The method of any one of Clauses 23-30, wherein the suggested medical device is a continuous positive airway pressure (CPAP) mask.

Clause 32: A method, comprising: receiving de-identified face data associated with a first patient, wherein the de-identified face data does not uniquely identify the first patient; identifying, based on a first identifier associated with the de-identified face data, patient data stored in a first data store; and associating the de-identified face data and the patient data.

Clause 33: The method of Clause 32, wherein the patient data corresponds to therapy data for the first patient, wherein the therapy data indicates patient compliance with one or more prescribed therapies.

Clause 34: The method of any one of Clauses 32-33, further comprising: determining, based on the therapy data, that the first patient has one or more issues with a prescribed medical device; and identifying a suggested medical device based on the de-identified face data.

Clause 35: The method of any one of Clauses 32-34, wherein the patient data corresponds to equipment data for the first patient, wherein the equipment data indicates an actual medical device that was provided to the first patient.

Clause 36: The method of any one of Clauses 32-35, further comprising: determining, based on the equipment data, that the actual medical device does not match a suggested medical device for the first patient; and generating an alert indicating that the suggested medical device and the actual medical device do not match.

Clause 37: The method of any one of Clauses 32-36, further comprising transmitting, to a provider that provided the actual medical device, a request for information relating to why the actual medical device was provided.

Clause 38: The method of any one of Clauses 32-37, further comprising transmitting, to the first patient, an indication that the actual medical device does not match the suggested medical device.

Clause 39: A system, comprising: a memory comprising computer-executable instructions; and one or more processors configured to execute the computer-executable instructions and cause the processing system to perform an operation in accordance with any one of Clauses 1-38.

Clause 40: A system, comprising means for performing a method in accordance with any one of Clauses 1-38.

Clause 41: A non-transitory computer-readable medium comprising computer-executable instructions that, when executed by one or more processors of a processing system, cause the processing system to perform a method in accordance with any one of Clauses 1-38.

Clause 42: A computer program product embodied on a computer-readable storage medium comprising code for performing a method in accordance with any one of Clauses 1-38.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word “exemplary” means “serving as an example, instance, or illustration.” Any aspect described herein as “exemplary” is not necessarily to be construed as preferred or advantageous over other aspects.

As used herein, a phrase referring to “at least one of” a list of items refers to any combination of those items, including single members. As an example, “at least one of: a, b, or c” is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term “determining” encompasses a wide variety of actions. For example, “determining” may include calculating, computing, processing, deriving, investigating, looking up (e.g., looking up in a table, a database or another data structure), ascertaining and the like. Also, “determining” may include receiving (e.g., receiving information), accessing (e.g., accessing data in a memory) and the like. Also, “determining” may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the de-identification component 120) or related data available in the cloud. For example, the de-identification component 120 could execute on a computing system in the cloud and de-identify user data. In such a case, the de-identification component 120 could de-identify user data such as face data, and store the de-identified data, identifying data, and/or other data at a storage location in the cloud. Doing so allows a user to access this information from any computing system attached to a network connected to the cloud (e.g., the Internet).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method comprising:

receiving face data for a first patient, wherein the face data is identifying of the first patient and is associated with a first identifier of the first patient;

de-identifying the face data;

determining a suggested medical device by processing at least one of the face data or the de-identified face data using a recommendation model;

identifying, based on the first identifier, therapy data stored in a first data store;

identifying, based on the first identifier, equipment data stored in a second data store, wherein the equipment data indicates an actual medical device that was provided to the first patient;

generating linked de-identified data by linking the suggested medical device, the therapy data, the equipment data, and the de-identified face data in a third data store using the first identifier, wherein the linked de-identified data does not include the face data; and facilitating access to the linked de-identified data without enabling access to the face data.

2. The method of claim 1, wherein:

the de-identified face data comprises one or more facial measurements of the first patient, and wherein the de-identified face data does not uniquely identify the first patient, and the method further comprises storing the face data in a fourth data store discrete from the first, second, and third data stores.

3. The method of claim 1, wherein de-identifying the face data comprises:

determining a set of coordinates for a set of facial landmarks based on the face data; and normalizing the set of coordinates using a normalization value.

4. The method of claim 1, wherein:

the face data comprises a three-dimensional (3D) mesh of a face of the first patient, and the method further comprises de-identifying the face data prior to identifying the therapy data or the equipment data.

5. The method of claim 4, wherein:

de-identifying the face data comprises extracting one or more facial measurements based on the 3D mesh, the one or more facial measurements do not uniquely identify the first patient, and the method further comprises:

linking the one or more facial measurements with the suggested medical device, therapy data, and equipment data, wherein the face data is not linked to the therapy data or equipment data.

6. The method of claim 4, wherein:

de-identifying the face data comprises generating a morphed 3D mesh based on the 3D mesh, wherein the morphed 3D mesh does not uniquely identify the first patient, and the method further comprises:

linking the morphed 3D mesh with the suggested medical device, therapy data, and equipment data, wherein the face data is not linked to the therapy data or equipment data.

7. The method of claim 6, wherein generating the morphed 3D mesh comprises morphing the 3D mesh based on principal component analysis (PCA) and a set of statistical shape models for human faces.

8. The method of claim 1, further comprising:

outputting, via a graphical user interface (GUI), the linked suggested medical device, therapy data, and equipment data.

9. The method of claim 1, further comprising:

determining, based on the linked suggested medical device and equipment data, that the suggested medical device and actual medical device do not match; and generating an alert indicating that the suggested medical device and the actual medical device do not match.

10. The method of claim 9, further comprising:

transmitting, to a provider that provided the actual medical device, a request for information relating to why the actual medical device was provided.

11. The method of claim 9, further comprising transmitting, to the first patient, an indication that the actual medical device does not match the suggested medical device.

12. The method of claim 1, further comprising:

determining, based on the linked therapy data and equipment data, that the first patient has one or more issues with the actual medical device; and refining the recommendation model based on the one or more issues.

13. The method of claim 1, further comprising selecting a first measurement technique, of a plurality of measurement techniques, for generating face data based at least in part on the linked suggested medical device, the therapy data, and the equipment data.

14. The method of claim 1, wherein the face data was received in response to transmitting, to the first patient, a request to provide the face data.

15. The method of claim 1, wherein the suggested medical device is a continuous positive airway pressure (CPAP) mask.

16. A method, comprising:

accessing, by a user device, a patient survey via a provided link for a first patient;

providing a set of responses for the patient survey, wherein the set of responses facilitate selection of a mask for the first patient;

generating identifying face data by performing a facial scan of the first patient using one or more cameras of the user device;

generating de-identified face data based on de-identifying the identifying face data;

transmitting the de-identified face data, along with the set of responses, to a mask selection component without providing access to the identifying face data, wherein:

the mask selection component uses the de-identified face data and set of responses to select the mask for the first patient;

linked de-identified data is generated by linking the de-identified face data with therapy data for the first patient and equipment data for the first patient;

the identifying face data is not linked with the therapy data or the equipment data; and access to the linked de-identified data is facilitated without enabling access to the identifying face data.

17. The method of claim 16, wherein:

the de-identified face data comprises one or more facial measurements of the first patient that do not uniquely identify the first patient, the one or more facial measurements are generated by the user device by processing one or more images, captured by the one or more cameras of the user device, using one or more machine learning models, and the one or more images are not transmitted to the mask selection component.

18. The method of claim 16, the method further comprising:

determining a set of coordinates for a set of facial landmarks based on the face data; and normalizing the set of coordinates using a normalization value.

19. The method of claim 16, wherein:

the identifying face data comprises a three-dimensional (3D) mesh of a face of the first patient.

20. The method of claim 19, wherein:

de-identifying the identifying face data comprises extracting one or more facial measurements based on the 3D mesh, and the de-identified face data correspond to the one or more facial measurements.

21. The method of claim 19, wherein:

de-identifying the identifying face data comprises generating a morphed 3D mesh based on the 3D mesh, and the de-identified face data correspond to the morphed 3D mesh.

22. A system, comprising:

a user device configured to perform an operation comprising:

collecting, from a first patient, survey data; and determining, using on one or more imaging devices, face data for the first patient;

a first data store configured to store the survey data and the face data for the first patient;

a second data store configured to store therapy data for the first patient, wherein the therapy data indicates patient compliance with one or more prescribed therapies;

a third data store configured to store equipment data for the first patient, wherein the equipment data indicates an actual facial mask provided to the first patient; and a computing device configured to perform an operation comprising:

selecting a suggested facial mask based on the face data;

de-identifying the face data, such that the face data does not uniquely identify the first patient;

generating linked de-identified data by linking the de-identified face data, the therapy data, the equipment data, and the suggested facial mask in a fourth data store, wherein the linked de-identified data does not include the face data; and facilitating access to the linked de-identified data without providing access to the face data.

* * * * *